United States Patent [19]
Mallinson et al.

[11] Patent Number: 6,159,432
[45] Date of Patent: Dec. 12, 2000

[54] CONVERSION METHOD FOR GAS STREAMS CONTAINING HYDROCARBONS

[75] Inventors: Richard G. Mallinson; Lance Lobban, both of Norman, Okla.; Chang-jun Liu, Tianjin, China

[73] Assignee: The Board of Regents of the University of Oklahoma, Norman, Okla.

[21] Appl. No.: 09/006,739

[22] Filed: Jan. 14, 1998

Related U.S. Application Data

[63] Continuation-in-part of application No. 08/813,813, Mar. 6, 1997, abandoned.
[60] Provisional application No. 60/035,900, Jan. 23, 1997.

[51] Int. Cl.[7] .................................................. B01J 19/08
[52] U.S. Cl. ...................................... 422/186.04; 204/165
[58] Field of Search .................................... 204/164, 165; 422/186.04, 186.26

[56] References Cited

U.S. PATENT DOCUMENTS

| | | | |
|---|---|---|---|
| 3,205,162 | 9/1965 | MacLean | 204/165 |
| 4,727,207 | 2/1988 | Paparizos et al. | 585/415 |
| 5,015,799 | 5/1991 | Walker et al. | 585/500 |
| 5,019,355 | 5/1991 | Sackinger | 422/186.04 |
| 5,077,446 | 12/1991 | Kolts et al. | 585/500 |
| 5,211,919 | 5/1993 | Conrad | 422/186.07 |
| 5,427,747 | 6/1995 | Kong et al. | 422/186 |
| 5,609,736 | 3/1997 | Yamamoto | 204/164 |
| 5,817,218 | 10/1998 | Hayashi et al. | 204/164 |
| 5,877,395 | 3/1999 | Emery | 588/900 |

*Primary Examiner*—Kishor Mayekar
*Attorney, Agent, or Firm*—Dunlap, Codding & Rogers, P.C.

[57] ABSTRACT

An apparatus and a method of using the apparatus are provided for converting a gas stream containing hydrocarbons to a reaction product containing effluent molecules having at least one carbon atom, having at least one interior surface and at least one exterior surface, a first electrode and a second electrode with the first and second electrodes being selectively movable in relation to each other and positioned within the housing so as to be spatially disposed a predetermined distance from each other, a plasma discharge generator between the first and second electrodes, gas stream introducer and a collector for collecting the reaction product effluent produced by the reaction of the gas stream containing hydrocarbons with the plasma discharge between the first and second electrodes.

11 Claims, 12 Drawing Sheets

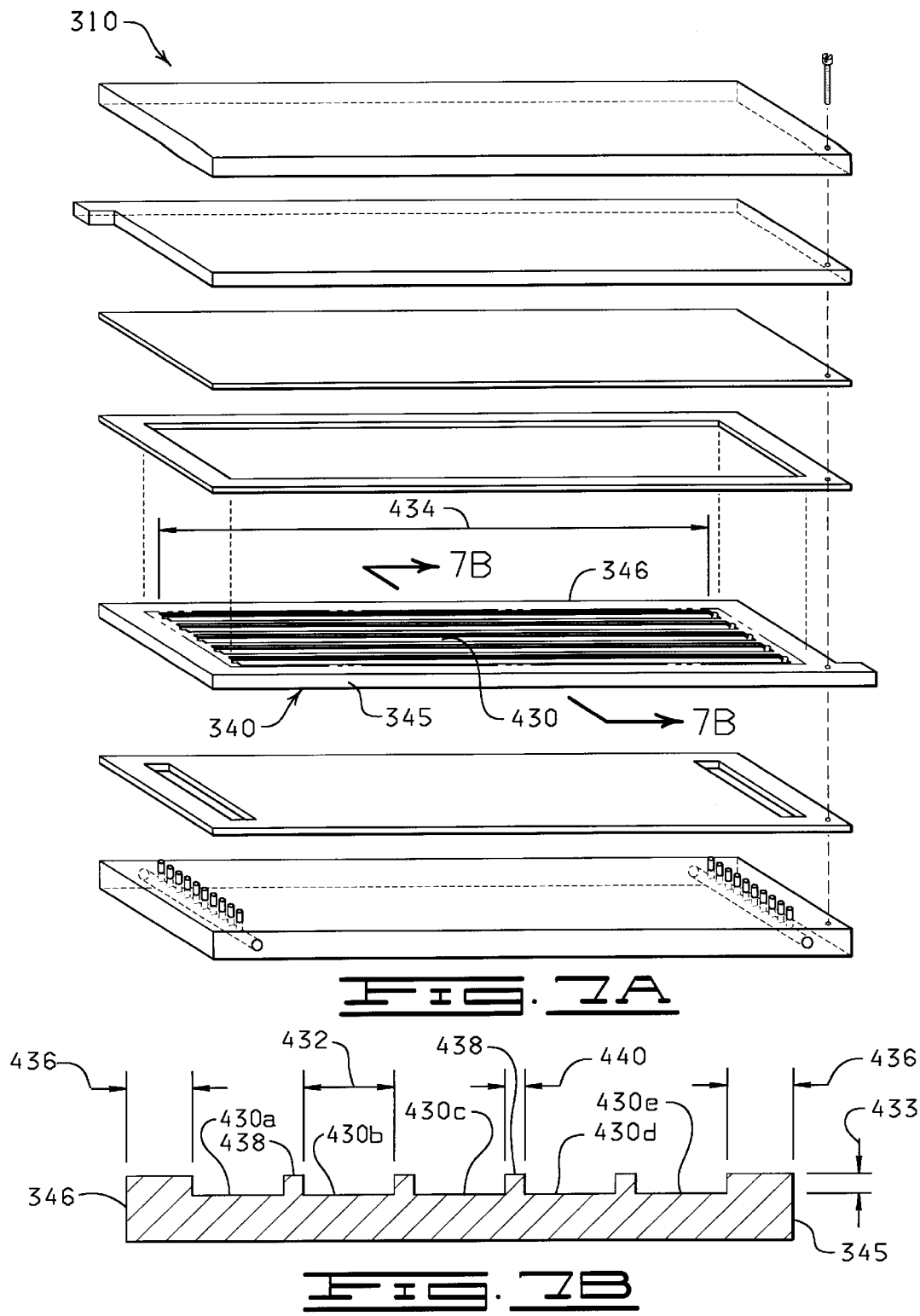

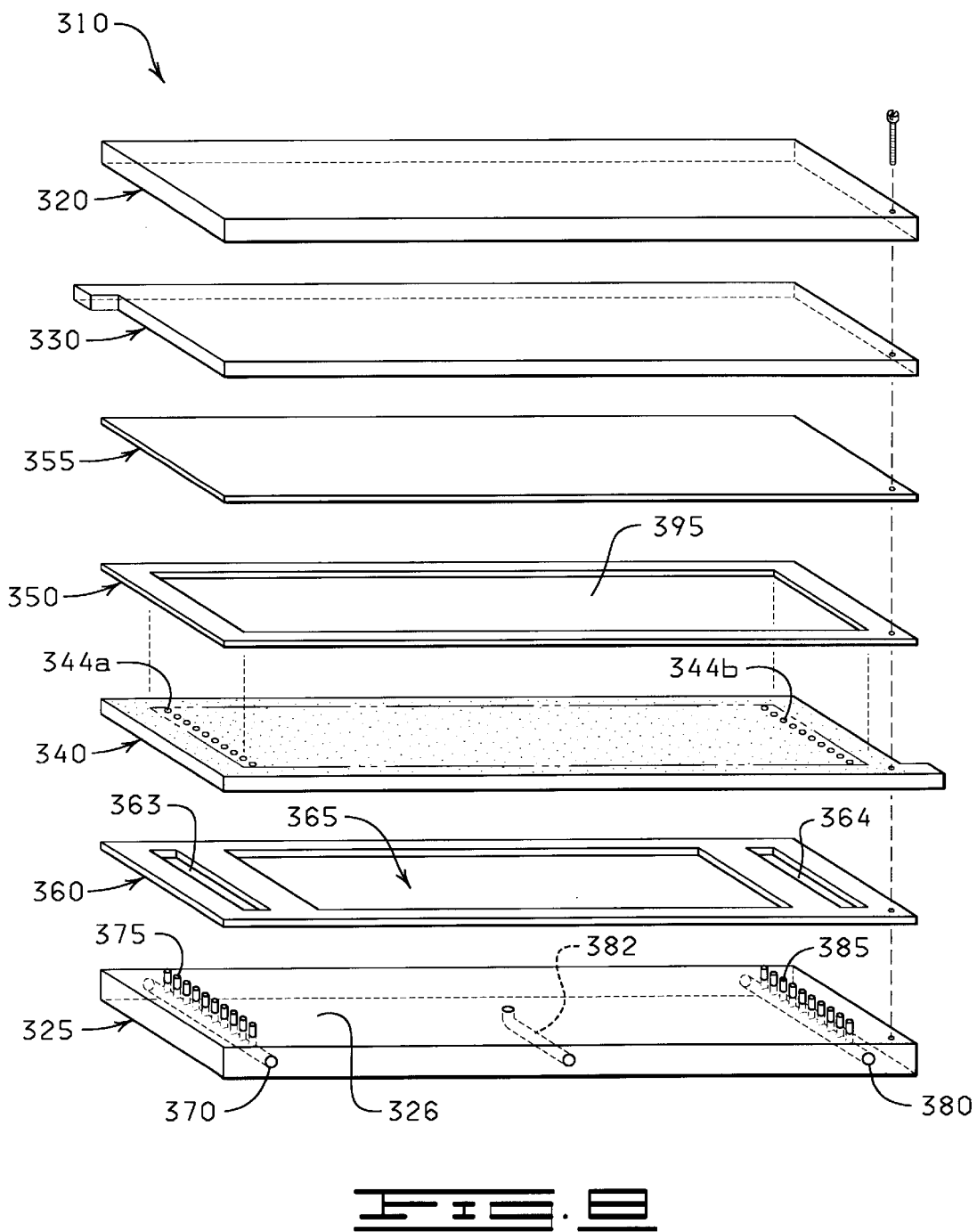

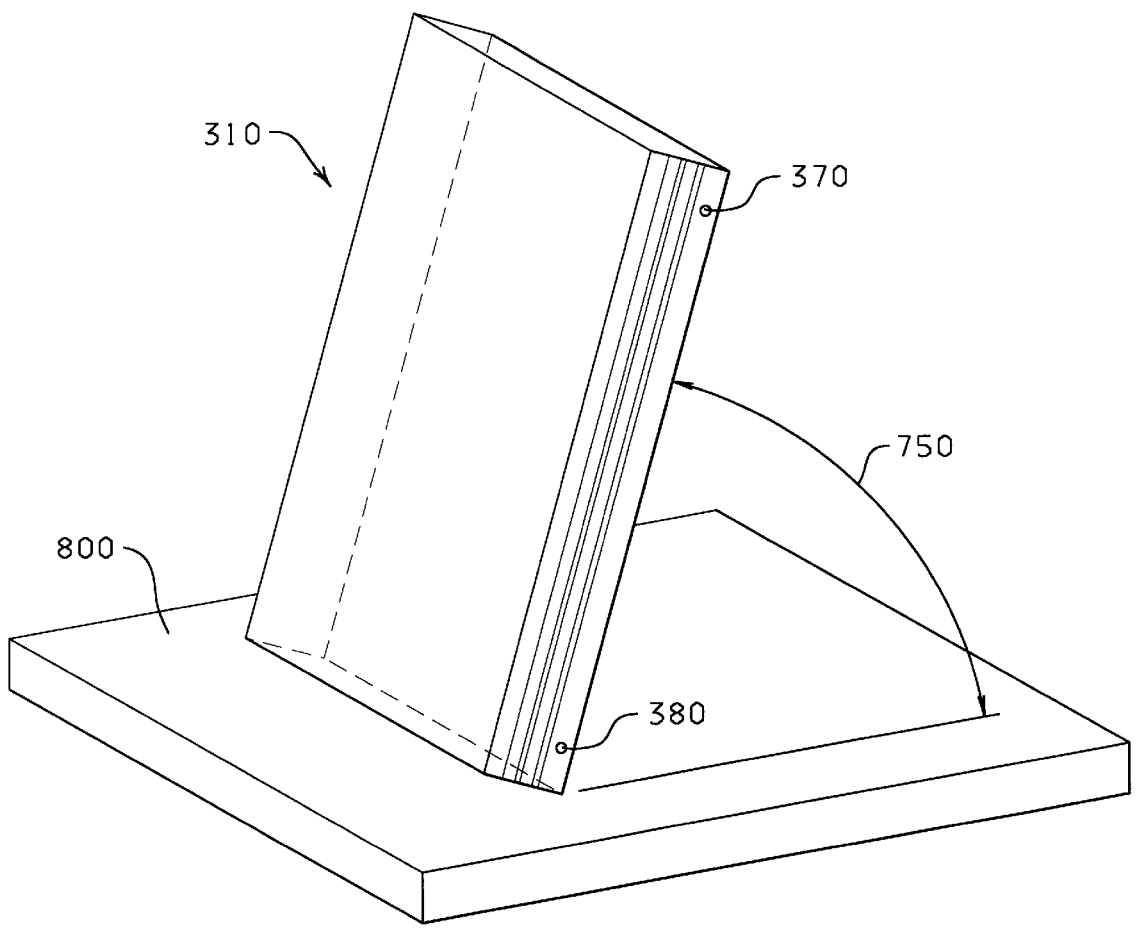

CONVERSION METHOD FOR GAS STREAMS CONTAINING HYDROCARBONS

CROSS REFERENCE TO RELATED APPLICATIONS

This application is a continuation-in-part application of U.S. patent application Ser. No. 08/813,813, filed Mar. 6, 1997, now abandoned and which claims the benefit of U.S. Provisional Application Ser. No. 60/035,900, filed Jan. 23, 1997.

FEDERALLY SPONSORED RESEARCH OR DEVELOPMENT

This invention was developed through assistance with the U.S. Department of Energy, under contract number DE-FG21-94MC31170. The Government has certain rights in this invention.

BACKGROUND OF THE INVENTION

1. Field of the Invention

The present invention relates in general to an apparatus and method for converting a gas stream containing hydrocarbons to a reaction product containing at least one carbon atom, and more particularly to an apparatus and method for converting a gas stream containing hydrocarbons, such as methane gas, to a reaction product containing at least one carbon atom by reacting the hydrocarbon containing gas stream with a plasma discharge generated between two electrodes.

2. Background of the Art

Natural gas is an abundant resource available worldwide. Methane gas oftentimes accounts for over 90 mole percent of the hydrocarbon composition of natural gas. Although methane gas is readily available, the transportation, storage, and conversion of methane gas is in many cases not economically feasible. Furthermore, higher level hydrocarbons, such as ethane and ethylene, are more economically desirable than methane. Demands for methanol and ethylene, two target products of natural gas conversion, are large and increasing. In particular, the possibility of producing ethylene from methane has attracted intense industrial and academic interest. However, even with the low cost of natural gas, current methane-to-methanol or methane-to-ethylene technologies are in many cases simply too expensive.

Methane conversion has historically and currently involved steam reformation of methane into a mixture of carbon monoxide and hydrogen with the resultant conversion of the carbon monoxide and hydrogen to oxygenates or higher level hydrocarbons. The steam reformation process is, however, highly expensive and requires a large energy input and elevated operational pressures. Direct oxidative coupling of methane (OCM) to higher level hydrocarbons lowers the cost and energy requirements of steam reformation. The primary limitation of oxidative coupling methane conversion is the fact that methane molecules are highly stable in comparison to any of the products formed during the reaction. The energy required to break the carbon-hydrogen bond in methane is quite high. Moreover, direct methane conversion to higher level hydrocarbons is thermodynamically unfavorable below 800 degrees Celsius. This thermodynamic instability can be overcome through the addition of oxygen; however, the addition of oxygen favors the formation of carbon oxides, such as carbon monoxide and carbon dioxide, rather than the formation of higher level hydrocarbons such as ethane or ethylene.

Therefore, although the conversion of methane by oxidative coupling (OCM) has become an active and productive area of research in the past several years, researchers have been unable to devise a simple and economical system which converts methane into higher level hydrocarbons in a one step process at or about atmospheric pressure. Research performed in the early part of the twentieth century on methane in an electric discharge reactor has led to patents being filed on several processes; namely, the production of various aldehydes from methane and carbon dioxide as well as the formation of formaldehyde from methane and oxygen. A large number of chemicals have been prepared by electrochemical synthesis methods, including via plasma reactions. The potential of clean, low-cost, highly selective and energy-efficient synthesis has been found to exist in those processes involving organic electrosynthesis and plasma-catalytic synthesis techniques. In these plasma techniques, free radicals generated by excitation, dissociation and ionization of gas molecules are essential for the subsequent free radical reactions.

The present invention contemplates the conversion of methane in a high pressure (from about one atmosphere to more than 10 atmospheres) and non-thermal plasma generated by corona discharge. The corona discharge encourages the formation of active methane species by the reaction of methane with charged oxygen or other species created in the corona discharge.

Thus, it is an object of the present invention to provide an apparatus for the one step conversion of a hydrocarbon containing gas stream such as natural gas, to higher level hydrocarbons from about atmospheric pressure to more than 10 atmospheres.

It is a further object of the present invention to provide a method for the conversion of a hydrocarbon containing gas stream, such as natural gas, into higher level hydrocarbons through a one step reaction.

It is yet a further object of the present invention to provide an apparatus and method for the conversion of a hydrocarbon containing gas stream, such as natural gas, into higher level organics containing at least one oxygen atom.

It is still another object of the present invention to provide an apparatus and method for the conversion of a hydrocarbon containing gas stream, into higher level hydrocarbons wherein the apparatus contains a catalyst capable of activating the natural gas, and more particularly methane, for coupling at a relatively low temperature from about ambient temperature to 100–300 degrees centigrade.

These and other objects of the present invention will become apparent in light of the present specification, claims, and drawings.

SUMMARY OF THE INVENTION

The present invention comprises an apparatus for converting a gas stream containing hydrocarbons to a reaction product containing effluent molecules having at least one carbon atom. The apparatus has a housing having at least one interior surface and at least one exterior surface, a first electrode and a second electrode with the first and second electrodes being selectively movable in relation to each other and further positioned within the housing so as to be spatially disposed a predetermined distance from each other, a means for producing a plasma discharge between the first and second electrodes, a means for passing the gas stream containing hydrocarbons between the first and second electrodes, and a means for collecting the reaction product effluent produced by the reaction of the gas stream containing hydrocarbons with the plasma discharge between the first and second electrodes.

In an embodiment the apparatus further includes at least one spacing member operably associated with at least one of the first and second electrodes in order to spatially maintain the first and second electrodes at the predetermined distance. The spacing member may be a dielectric material. In the embodiment where the spacing member is a dielectric material, the dielectric material may be glass. Furthermore, the dielectric material may be operably associated with at least one of the first and second electrodes. In another embodiment, the spacing member is a non-conducting spacer having a passageway extending therethrough for allowing the passage and collection of the gas stream containing hydrocarbons between the first and second electrodes. In yet another embodiment, the spacing member is a dielectric material and a non-conducting spacer.

In another embodiment the apparatus also includes means for condensing the effluent. The effluent may be a gas, a liquid, or a mixture of a gas and a liquid.

In an embodiment, the apparatus further includes means for condensing the reaction product produced by the reaction of the gas stream containing hydrocarbons with the plasma discharge. The reaction product condensing means is disposed within the housing. The reaction product condensing means may be provided with channels extending along at least a portion of the interior surface of the housing for thereby collecting the condensed reaction products. The reaction product condensing means may also be a liquid substantially adjacent the exterior surface of the housing or the reaction product condensing means may be a membrane operably attached to at least a portion of the interior surface of the housing, such that the reaction product flows through at least a portion of the membrane. Indeed, the reaction product condensing means may include channels extending along at least a portion of the interior surface of the housing for collecting the condensed reaction product, a liquid flowing substantially adjacent the exterior surface of the housing, and a membrane operably attached to at least a portion of the interior surface of the housing, such that the reaction product flows through at least a portion of the membrane.

In another embodiment the reaction product is absorbable and the apparatus has means for absorbing the absorbable reaction product which is produced by the reaction of the gas stream containing hydrocarbons with the plasma discharge. The absorbing means may be a liquid capable of absorbing the absorbable reaction product and in an embodiment the liquid is a solution of an effective amount of a silver salt.

In yet another embodiment the reaction product is adsorbable and the apparatus has means for adsorbing the adsorbable reaction product produced by the reaction of the gas stream containing hydrocarbons with the plasma discharge. The adsorbing means may be a solid capable of adsorbing the adsorbable reaction product and in an embodiment the solid is an effective amount of a zeolite. In yet a further embodiment, the zeolite may have been treated in a manner so as to affect its adsorption properties. One such treatment would be to treat the zeolite with a salt, although one of ordinary skill in the art would appreciate that any modified zeolite capable of adsorbing the adsorbable reaction product is contemplated for use with this invention.

In yet another embodiment the apparatus has a layer of material operably connected to at least one of the first and second electrodes. The layer of material is a material capable of modifying the reaction of the stream of gas containing hydrocarbons with the plasma discharge. The layer of material may be a single metal oxide selected from the group consisting of $CaO$, $PbO$, $Sm_2O_{31}$, and $La_2O_3$. The layer of material may also be a multiple metal oxide selected from the group consisting of $Li/MgO$, $Sr/La_2O_3$, $Sm_2O_3$, $NaOH/CaO$, $Na_2O/Pr_2O_3$, $Ca/Ni/K$ oxide, $La_2O_3$, $Bi_2O_3$—$K_2CO_3$—$Al_2O_3$. The layer of material may also be a perovskite selected from the group consisting of $LaMnO_3$, $LaAlO_3$, $SrTiO_3$, $CrLa_{1-x}Sr_xO_3$, and $BaPb_{1-x}Bi_xO_3$. The layer of material may also be a zeolite selected from the group consisting of mordenite, faujasite, Y or X zeolite, and ZSM5, and as previously stated with regard to the adsorbable zeolite, any of these zeolites may also be chemically or physically modified.

The present invention also comprises an apparatus for converting a gas stream containing hydrocarbons to a reaction product effluent containing molecules having at least one carbon atom and at least a portion of the molecules having at least one carbon atom and at least a portion of the molecules containing an oxygen atom. The apparatus has a housing having at least one interior surface and at least one exterior surface, a first electrode and a second electrode with the first and second electrodes being selectively movable in relation to each other and further positioned within the housing so as to be spatially disposed a predetermined distance from each other, a means for producing a plasma discharge between the first and second electrodes, a means for passing the gas stream containing hydrocarbons between the first and second electrodes, and a means for collecting the reaction product effluent produced by the reaction of the gas stream containing hydrocarbons with the plasma discharge between the first and second electrodes.

The present invention further comprises a method for converting a gas stream containing hydrocarbons to a reaction product effluent containing molecules having at least one carbon atom. The method comprises the steps of (1) providing an apparatus having a housing, the housing having at least one interior surface and at least one exterior surface, a first electrode and a second electrode with the first and second electrodes being selectively movable in relation to each other and further positioned within the housing so as to be spatially disposed a predetermined distance from each other, a means for producing a plasma discharge between the first and second electrodes, a means for passing the gas stream containing hydrocarbons between the first and second electrodes, and a means for collecting the reaction product effluent produced by the reaction of the gas stream containing hydrocarbons with the plasma discharge between the first and second electrodes; (2) producing a plasma discharge between the first and second electrodes; (3) passing a gas stream containing hydrocarbons between the first and second electrodes, wherein the plasma discharge causes the stream of gas containing hydrocarbons to be converted to the reaction product effluent containing hydrocarbons having at least two carbon atoms; and (4) collecting the reaction product effluent.

In an embodiment of the method, the method comprises an additional step of providing at least one spacing member operably associated with at least one of the first and second electrodes in order to spatially maintain the first and second electrodes at the predetermined distance. The spacing member may be a dielectric material. In the embodiment where the spacing member is a dielectric material, the dielectric material may be glass.

Furthermore, the dielectric material may be operably associated with at least one of the first and second electrodes. In another embodiment, the spacing member is a non-conducting spacer having a passageway extending therethrough for allowing the passage and collection of the gas stream containing hydrocarbons between the first and second electrodes. In yet another embodiment, the spacing member is a dielectric material and a non-conducting spacer.

In another embodiment of the method, the method also includes providing a means for condensing the effluent. The effluent may be a gas, a liquid, or a mixture of a gas and a liquid.

In an embodiment of the method, the method further includes providing a means for condensing the reaction product produced by the reaction of the gas stream containing hydrocarbons with the plasma discharge. The reaction product condensing means is disposed within the housing. The reaction product condensing means may be provided with channels extending along at least a portion of the interior surface of the housing for thereby collecting the condensed reaction products. The reaction product condensing means may also be a liquid substantially adjacent the exterior surface of the housing or the reaction product condensing means may be a membrane operably attached to at least a portion of the interior surface of the housing, such that the reaction product flows through at least a portion of the membrane. Indeed, the reaction product condensing means may include channels extending along at least a portion of the interior surface of the housing for collecting the condensed reaction product, a liquid flowing substantially adjacent the exterior surface of the housing, and a membrane operably attached to at least a portion of the interior surface of the housing, such that the reaction product flows through at least a portion of the membrane.

In another embodiment of the method, the method comprises the step of providing means for absorbing an absorbable reaction product which is produced by the reaction of the gas stream containing hydrocarbons with the plasma discharge. The absorbing means may be a liquid capable of absorbing the absorbable reaction product and in an embodiment the liquid is a solution of an effective amount of a silver salt.

In yet another embodiment of the method, the method comprises the step of providing means for adsorbing an adsorbable reaction product produced by the reaction of the gas stream containing hydrocarbons with the plasma discharge. The adsorbing means may be a solid capable of adsorbing the adsorbable reaction product and in an embodiment the solid is an effective amount of a zeolite. In yet a further embodiment, the zeolite may have been treated in a manner so as to affect its adsorption properties. One such treatment would be to treat the zeolite with a salt, although one of ordinary skill in the art would appreciate that any modified zeolite capable of adsorbing the adsorbable reaction product is contemplated for use with this invention.

In yet another embodiment of the method, the method includes the step of providing a layer of material operably connected to at least one of the first and second electrodes. The layer of material is a material capable of modifying the reaction of the stream of gas containing hydrocarbons with the plasma discharge. The layer of material may be a single metal oxide selected from the group consisting of Cao, Pbo, $Sm_2O_3$, and $La_2O_3$. The layer of material may also be a multiple metal oxide selected from the group consisting of Li/MgO, $Sr/La_2O_3$, $Sm_2O_3$, NaOH/CaO, $Na_2O/Pr_2O_3$, Ca/Ni/K oxide, $La_2O_3$, $Bi_2$—$O_3K_2CO_3$—$Al_2O_3$. The multiple metal oxide layer of material may also be a perovskite selected from the group consisting of $LaMnO_3$, $LaAlO_3$, $SrTiO_3$, $CrLa_{1-x}Sr_xO_3$, and $BaPb_{1-x}Bi_xO_3$. The layer of material may also be a zeolite selected from the group consisting of mordenite, faujasite, Y or X zeolite, and ZSM5, and as previously stated with regard to the adsorbable zeolite, any of these zeolites may also be chemically or physically modified.

The present invention also comprises a method for converting a gas stream containing hydrocarbons to a reaction product effluent containing molecules having at least one carbon atom and at least some of the molecules containing an oxygen atom. The method comprises the steps of (1) providing an apparatus having a housing, the housing having at least one interior surface and at least one exterior surface, a first electrode and a second electrode with the first and second electrodes being selectively movable in relation to each other and further positioned within the housing so as to be spatially disposed a predetermined distance from each other, a means for producing a plasma discharge between the first and second electrodes, a means for passing the gas stream containing hydrocarbons between the first and second electrodes, and a means for collecting the reaction product effluent produced by the reaction of the gas stream containing hydrocarbons with the plasma discharge between the first and second electrodes; (2) producing a plasma discharge between the first and second electrodes; (3) passing a gas stream containing hydrocarbons between the first and second electrodes, wherein the plasma discharge causes the stream of gas containing hydrocarbons to be converted to the reaction product effluent containing hydrocarbons having at least two carbon atoms; and (4) collecting the reaction product effluent.

BRIEF DESCRIPTION OF THE DRAWINGS

FIG. 7A of the drawings is an exploded pictorial representation of the methane conversion apparatus of FIG. 5B, showing, in particular, channels in the second electrode for absorbing a reaction product.

FIG. 7B of the drawings is a cross-sectional representation along line 7B—7B of FIG. 7A, showing, in particular, the channels for absorbing a reaction product.

FIG. 8 of the drawings is an exploded pictorial representation of the methane conversion apparatus of FIG. 5B, showing, in particular, a porous first or second electrode and a passage extending through the spacing means.

FIG. 9 of the drawings is a side pictorial representation of the methane conversion apparatus of FIG. 5, showing, in particular, the position and degree of incline of the methane conversion apparatus relative to a support surface.

DETAILED DESCRIPTION OF THE INVENTION

Figure 1A:
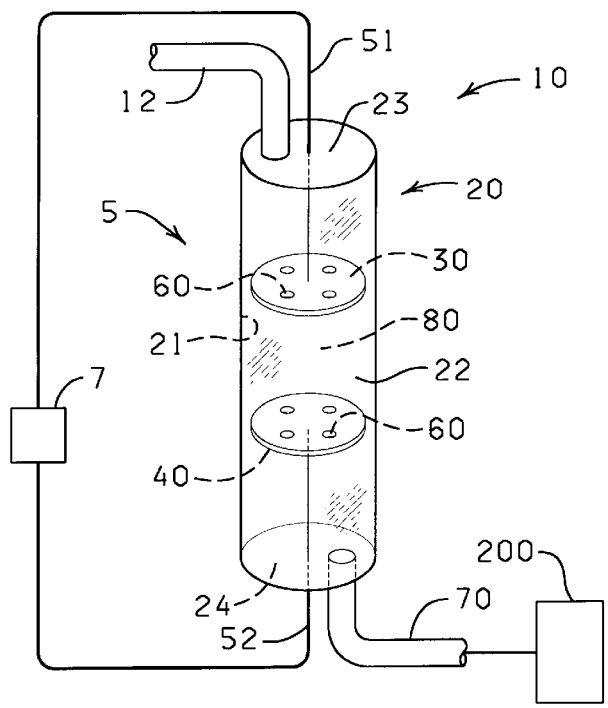
FIG. 1A of the drawings is a pictorial representation of a methane conversion apparatus embodying the present invention showing the housing, the first and second electrodes, means for producing a plasma discharge, means for passing a gas stream between the first and second electrodes, and means for collecting the reaction product effluent.

Before explaining at least one embodiment of the invention in detail, it is to be understood that the invention is not limited in its application to the details of construction and the arrangements of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Figure 1B:
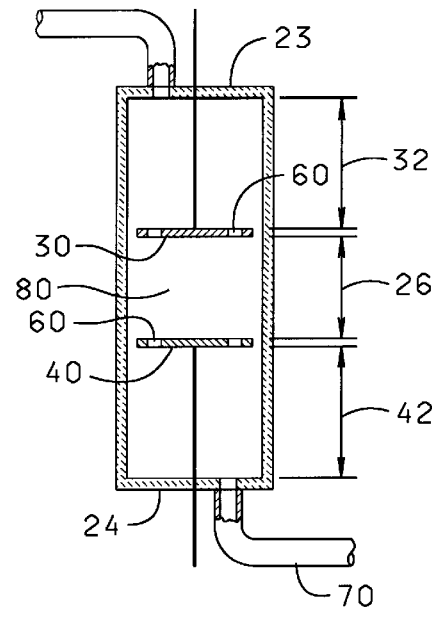
FIG. 1B of the drawings is a cross-sectional representation of the methane conversion apparatus of FIG. 1A, showing, in particular, the relative spacing of the first and second electrodes within the apparatus housing.

One embodiment of the present gas stream conversion apparatus 10 is shown in FIGS. 1A and 1B, as comprising housing 20, having an interior surface 21 and an exterior surface 22, a first end 23, a second end 24, a plasma discharge assembly 5 including a first electrode 30 extending a distance 32 from the first end 23, a second electrode 40 extending a distance 42 from the second end 24 and an adjustable distance 26 from first electrode 30, and a collecting assembly 70. It is preferable that housing 20 be fabricated from a crystalline material such as quartz, although one of skill in the art would understand that housing 20 may be fabricated from any suitable non-conductive material such as glass or plastic. It will also be understood that housing 20 may be fabricated from a conductive material if housing interior surface 21 is coated with a non-conductive material or laminated with a non-conductive material. Gas stream conversion apparatus 10 may also include a temperature regulator assembly (not shown) operably associated with housing 20 so as to regulate the temperature within housing 20. The plasma discharge assembly 5 comprises first and second electrodes 30, 40, a first lead 51 connected to first electrode 30 and a second lead 52 connected to second electrode 40 and a power source 7 connected to at least one of the first and second electrodes 30, 40.

Gas stream conversion apparatus 10 is used in the conversion of a gas stream containing hydrocarbons (referred to hereinafter as the "gas stream") to molecules having at least one carbon atom and preferably to $C_2$ (two carbon) hydrocarbons such as ethane or ethylene. In an embodiment, the gas stream will contain primarily methane in the form of natural gas. Whether natively contained or specifically added, it will be appreciated that natural gas may contain numerous other constituents besides methane, such as oxygen, carbon dioxide, nitrogen, helium, carbon monoxide, hydrogen, and other hydrocarbons. The reaction of these other constituents, however, is either negligible or is complimentary within the gas stream conversion apparatus 10, so as to not significantly interfere or, alternatively, assist with the primary reaction of methane to $C_2$ hydrocarbons. The gas stream may also primarily contain higher level hydrocarbons such as ethane, propane and/or butane, to name but a few. Further, even when the gas stream primarily contains methane, other higher level hydrocarbons such as ethane, propane and/or butane may also be present. It is contemplated that through the use of the gas stream conversion apparatus 10, hydrocarbons contained within the gas stream may be converted to higher level hydrocarbons. For example, if methane is the primary constituent of the gas stream, it is found that the reaction of the methane within the gas stream conversion apparatus 10 produces a reaction product of primarily acetylene, ethane, or ethylene. Furthermore, an oxygen atom source such as gaseous $O_2$ (not shown) may also be introduced with the gas stream, if the gas stream may contain an effective amount of $O_2$, whereby the reaction product may comprise oxygen-containing compounds such as methanol or ethanol.

Gas stream conversion apparatus 10 further includes a gas introduction assembly 12 for introducing the gas stream into housing 20 at first end 23. Gas introduction assembly 12 may be any conduit, pipe, tank, or pump capable of introducing the gas stream into housing 20 at a constant pressure with the resultant effect that the pressure within housing 20 forces any reaction product effluent produced therein to exit the housing 20 via the collecting assembly 70. Gas introduction assembly 12 may also include a regulator or series of pumps and regulators capable of introducing the gas stream into gas stream conversion apparatus 10. It will also be understood to those of skill in the art that gas introduction assembly 12 may include any apparatus capable of introducing a gas stream into conversion apparatus 10, including a plurality of gas introduction assemblies each having the ability to introduce and regulate the flow of distinct gases or gas mixtures into conversion apparatus 10.

First electrode 30 and second electrode 40 are preferably fabricated from one or more materials capable of generating an electric field therebetween when an electric charge is applied to first and second electrodes 30, 40. In one version, first and second electrodes 30, 40 are fabricated from stainless steel and may be generally shaped, as shown in FIGS. 1A, 1B, 2A, and 2B, as disks having passageways, apertures, interstices, or channels 60 extending therethrough for allowing passage of the gas stream through the electrodes 30, 40. In an alternate version of the invention, as shown in FIGS. 3A and 3B, a conversion apparatus 10a is the same as apparatus 10 shown above except a first electrode 30a comprises a small diameter rod, needle or wire, rather than a disk. The distal end 31 of the electrode 30a is disposed a predetermined distance 26a away from the surface of second electrode 40 which faces electrode 30a. First and second electrodes 30a, 40 are selectively movable in relation to one another by varying the length of first and second leads 51 and 52, respectively, or by moving the position of electrodes 30a and 40 in any other suitable manner, thereby changing the position of either first or second electrodes 30a and 40, or by changing the position of both first and second electrodes 30a and 40 in relation to each other.

Although first and second electrodes 30, 40 (shown in FIGS. 1A and 1B) have been described as being fabricated from stainless steel, it will be understood by one of ordinary skill in the art that first and second electrodes 30, 40 may be fabricated from any material capable of generating an electric field therebetween when an electric current is applied to at least one of the first and second electrodes 30, 40. Furthermore, first electrode 30 may be fabricated from a different material than second electrode 40. Reaction zone 80 is the space within the housing 20 generally between first and second electrodes 30 and 40, wherein the gas stream introduced into the first end 23 of the housing 20 reacts with the electric field generated by first and second electrodes 30, 40. As noted above, first electrode 30 may comprise a plurality of passageways 60 extending therethrough for allowing the gas stream to freely pass through first electrode 30 to reaction zone 80. Similarly, second electrode 40 may comprise a plurality of passageways 60 extending therethrough for allowing the reaction product effluent to pass from reaction zone 80 through second electrode 40 toward reaction product effluent collecting assembly 70.

Reaction product collecting assembly 70 may comprise any conduit, pipe, tank, or separation assembly capable of withdrawing the reaction product effluent from the gas stream conversion apparatus 10. Reaction product collecting assembly 70 may also include a condenser, such as condenser 200. It will also be understood by those of skill in the art that reaction product collecting assembly 70 may include any apparatus capable of collecting, segregating, analyzing, and/or condensing a reaction product effluent, including a plurality of reaction product collecting assemblies each having the ability to withdraw, collect, analyze, segregate, and/or condense a reaction product effluent exiting gas stream conversion apparatus 10.

In one embodiment, first lead 51 may be connected to a power supply 7 thereby directing a voltage to first electrode 30, while second lead 52 may ground second electrode 40 to a voltage of zero, wherein the plasma discharge assembly induces the formation of a plasma discharge within the reaction zone 80 between first and second electrodes 30, 40. The electric field may be created by either a high voltage DC power supply or an AC power supply with a high voltage transformer. When DC power is applied, second electrode 40 is grounded and first electrode 30 is at either a positive potential (referred to as positive corona) or negative potential (referred to as negative corona). It is contemplated that the electric field will take the form of a plasma discharge.

Plasma is a fourth state of matter. This discharge plasma is generated by the application of an electric field between two points. Specifically, this discharge plasma produces negatively charged ions, among other charged species. Within a discharge plasma, chemical reactions can occur between the free electrons, ions and neutral species and molecules within a gas stream, while the gas itself remains at a relatively low temperature. This discharge plasma (or simply "plasma") is obtained when sufficient energy (higher than the ionization energy) is added to a gas, thereby causing ionization and the production of both ions and electrons. Plasma density (concentration of electrons and ions) is an important parameter in plasma processing. The efficiency of the processes occurring in the plasma and the reaction rates directly depend on the density of the charged particles. The electrons in the plasma are responsible for the transfer of energy from the external electric field. Therefore, high ion density generally increases the rates of reactions involving the ions. In any gas system, the plasma particles are in continuous motion and are constantly causing collisions therebetween.

Heat, electric fields, and electromagnetic radiation are the three principle sources of energy for plasma generation. A "cold" plasma is defined as plasma which is not in local thermodynamic equilibrium. For instance, the electrons can reach temperatures of $10^4$–$10^5$ K (1 10 eV), while the temperature of the gas, ($T_g$), can be at room temperature or below. Cold plasmas are usually excited (and electrically sustained) by direct current (DC), alternating current (AC), radio frequency (RF) or microwave (MV) power applied to a gas. Chemical reactions occurring within cold plasma are generally controlled by electron energies and gas temperature. Therefore, the type of discharge used to create the plasma is immaterial as long as the identical energies and temperatures can be achieved.

A DC discharge plasma is produced by applying a DC voltage between two conductive electrodes inserted into a gas. As the voltage applied to the gas in the discharge tube is gradually increased, the free electrons available are accelerated in the electric field, thereby gaining kinetic energy. Concomitantly, the electrons lose energy in collisions with either the atoms or molecules of gas. These discharge plasmas are relatively low power electrical discharges that take place at or above atmospheric pressure. The discharge is created by a strong electric field associated with small diameter wires, needles, or sharp edges on an electrode.

First and second electrodes 30, 40 are spatially positioned within the housing 20 in such a manner that when connected to an energy source, such as a DC energy source (not shown), the plasma discharge is created therebetween within reaction zone 80. The distance 26 between first and second electrodes 30, 40 may be varied by changing the length of either first or second leads 51, 52, respectively, or by changing the position of either electrode 30 or electrode 40, or both, in relation to each other in any suitable manner. Although in a version, the plasma discharge assembly has been disclosed as including a DC energy source, it will be understood that any energy source capable of producing a plasma discharge between first and second electrodes 30, 40 is contemplated for use. Examples of such other energy sources would be AC, RF, or MV energy sources.

Figure 2A:
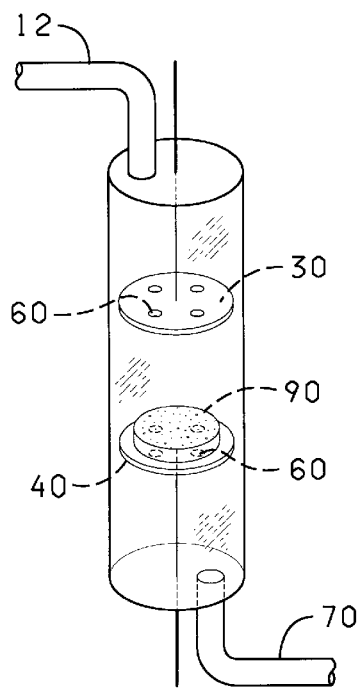
FIG. 2A of the drawings is a pictorial representation of the methane conversion apparatus of FIG. 1A, showing, in particular, a layer of material operably connected to at least one of the first and second electrodes.
Figure 2B:
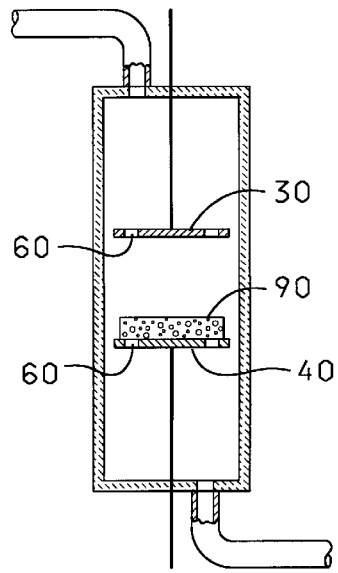
FIG. 2B of the drawings is a cross-sectional representation of the methane conversion apparatus of FIG. 2A, showing, in particular, the relative spacing of the first and second electrodes within the apparatus housing.
Figure 3A:
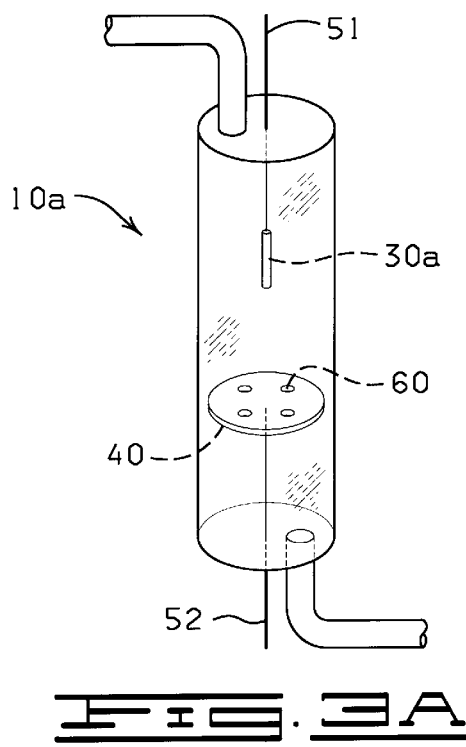
FIG. 3A of the drawings is a pictorial representation of the methane apparatus of FIG. 1A, showing, in particular, another embodiment of the first electrode.
Figure 3B:
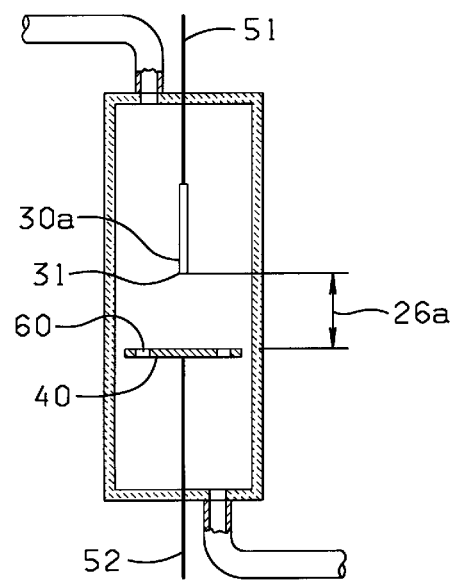
FIG. 3B of the drawings is a cross-sectional representation of the methane conversion apparatus of FIG. 3A, showing, in particular, the relative spacing of the first and second electrodes within the apparatus housing.

FIG. 2A shows a conversion apparatus 10 exactly the same as that shown in FIGS. 1A and 1B, except the gas stream conversion apparatus in FIG. 2A comprises an amount of a catalyst material 90 disposed upon, or otherwise associated with, a portion of the second electrode 40. Although preferably catalyst 90 is disposed on or otherwise associated with second electrode 40, catalyst 90 may alternatively be disposed on first electrode 30. Furthermore, it should be understood that catalyst material 90, while being shown as comprising a wafer operably associated with second electrode 40 in FIGS. 2A and 2B, may be a thin layer of material covering the entirety of second electrode 40, or catalyst material 90 may be operably associated within the structure of second electrode 40, and/or catalyst material 90 may be disposed in passageways 60 of second electrode 40. Therefore, one of skill in the art would understand that the placement of catalyst material 90 will not be limited to that shown in FIGS. 2A and 2B, and rather the placement of catalyst material 90 may vary in any regard, as long as the catalyst material 90 is capable of modifying the reaction of the gas stream within or in close proximity to the reaction zone 80.

Generally, catalysts used in OCM reactions may be classified as either reducible or irreducible metal oxides. Methane and oxygen may be fed alternately over reducible oxides and a redox mechanism for the reaction has been suggested for the production of $C_2$ products, wherein the metal oxide acts as both the reducing and oxidizing agent. Irreducible metal oxides, such as catalysts with rare-earth oxides, act as catalysts which are favorable for OCM. However, over both reducible and irreducible catalyst oxides, OCM in the absence of a corona discharge plasma still requires high reaction temperatures. A gas stream conversion apparatus 10 having a catalyst 90 on second electrode 40 may also encourage the selectivity of $C_2$ products at low temperatures; for example, by controlling the recombination of the activated species.

Catalyst 90 may be a single metal oxide or a multiple metal oxide. Single metal oxides contemplated for use include CaO, PbO, $Sm_2O_3$, and $La_2O_3$. Multiple metal oxides contemplated for use include Li/MgO, $Sr/La_2O_3$, $Sm_2O_3$, NaOH/CaO, $Na_2O/Pr_2O_3$, Ca/Ni/K oxide, $La_2O_3$, $Bi_2O_3$—$K_2CO_3$—$Al_2O_3$. Furthermore, catalyst 90 may include perovskites such as $LaMnO_3$, $LaAlO_3$, $SrTiO_3$, $CrLa_{1-x}Sr_xO_3$, and $BaPb_{1-x}Bi_xO_3$. Finally, it is contemplated that catalyst 90 be a zeolite, such as mordenite, faujasite, Y or X zeolite, and ZSM5, any of which may also be altered by various treatments. Although catalyst 90 has been disclosed as encompassing specific examples of single and multiple metal oxides, perovskites, and zeolites, it will be understood by a person of ordinary skill in the art that any material capable of hydrocarbon and/or organic oxygenate adsorption within or near the reaction zone 80 is contemplated for use as catalyst 90. Also, one of ordinary skill in the art would understand that the catalyst 90 may be in close proximity to reaction zone 80 and that catalyst 90 may also comprise differing catalysts placed at different positions within housing 20.

Figure 4A:
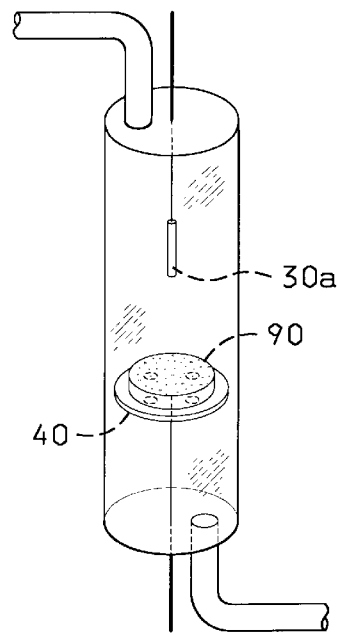
FIG. 4A of the drawings is a pictorial representation of the methane apparatus of FIG. 3A, showing, in particular, another embodiment of the first electrode.
Figure 4B:
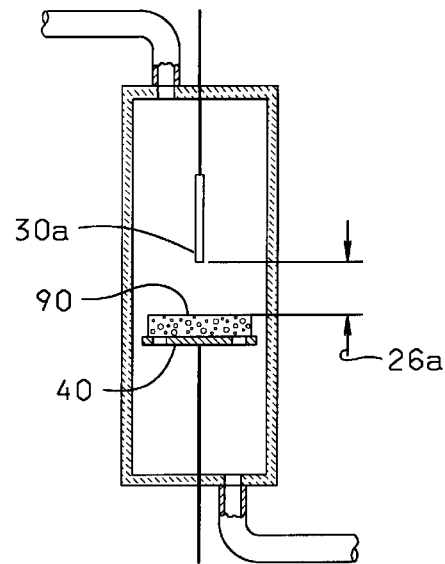
FIG. 4B of the drawings is a cross-sectional representation of the methane conversion apparatus of FIG. 4A, showing, in particular, the relative spacing of the first and second electrodes within the housing.
Figure 4C:
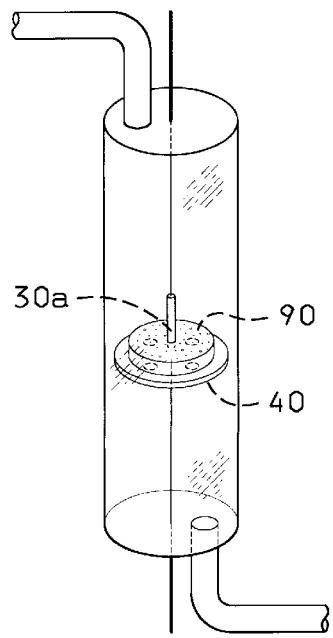
FIG. 4C of the drawings is a pictorial representation of the methane conversion apparatus of FIG. 4A, showing, in particular, the first electrode comprising a wire and extending a distance into the layer of material operably associated with the second electrode.
Figure 4D:
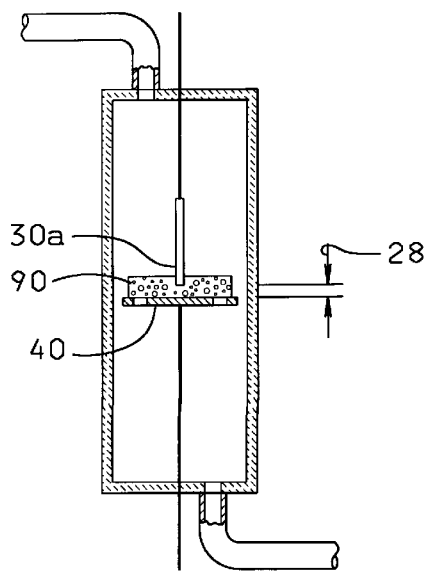
FIG. 4D of the drawings is a cross-sectional representation of the methane conversion apparatus of FIG. 4C, showing, in particular, the relative spacing of the first and second electrodes within the housing.

As shown in FIGS. 3A, 3B, 4A, 4B, 4C, and 4D, first electrode 30a may be disposed a predetermined distance 26a from second electrode 40 (as shown in FIGS. 3A and 4A). Alternatively, the first electrode 30a may come into contact with catalyst 90 on electrode 40 (as shown in FIG. 4C), or may extend into catalyst 90 a predetermined distance 28 (as shown in FIG. 4D). When first electrode 30a is positioned a distance 26a away from second electrode 40, the discharge created therebetween is generally referred to as remote. When first electrode 30a contacts catalyst 90 or extends into catalyst 90 a predetermined distance 28, the discharge created therebetween is generally referred to as direct.

In operation, a gas stream as defined above, preferably comprising methane, is introduced into the housing 20 of gas stream conversion apparatus 10 via the gas stream introduction assembly 12. The gas stream may also generally contain an amount of oxygen, hydrogen, carbon dioxide, or combinations thereof. The gas is forced through or past first electrode 30 by the pressure generated by gas stream introduction assembly 12. The gas stream flows through first electrode 30 via passageways 60 extending through first electrode 30. After passing through or past first electrode 30, the gas stream enters reaction zone 80, where it encounters a discharge plasma (not shown) generated by first and second electrodes 30, 40 within reaction zone 80 by a power source 7 connected to the first and/or second electrodes 30, 40. The gas stream reacts with the discharge plasma generated within reaction zone 80, thereby producing a reaction product. The reaction product will contain higher level hydrocarbons, some of which may contain an oxygen atom. Preferably, the reaction product will contain $C_2$ hydrocarbons, such as acetylene, ethane, and ethylene.

If the gas conversion apparatus 10 contains a catalyst disposed on an electrode, such as catalyst 90 in FIG. 2A, the reaction of the gas stream containing hydrocarbons with the discharge plasma generated between first and second electrodes 30, 40 will be affected in the manner described hereinabove. Namely, the catalyst 90 will alter the conversion reaction and/or product selectivity.

The reaction product and any remaining unreacted hydrocarbons from the gas stream containing hydrocarbons will thereafter be forced out of reaction zone 80 by the pressure created by gas stream introduction assembly 12. The reaction product and remaining unreacted hydrocarbons are forced through passageways 60 in second electrode 40 or past second electrode 40 toward reaction product effluent collecting assembly 70. The reaction product may be a gas, a liquid or a combination of a gas and liquid. The reaction product will generally be a liquid if the temperature within gas stream conversion apparatus 10 is below that of the condensation point of the reaction product. Therefore, reaction product effluent collecting assembly 70 may be an outlet tube, pipe or conduit capable of allowing the reaction product to exit the gas stream conversion apparatus 10. Reaction product effluent collecting assembly 70 may also be connected to an analysis assembly (not shown) for the quantitative analysis of the reaction product. Furthermore, the reaction product effluent collecting assembly 70 may include a condensing assembly 200 for condensing the reaction product, such as condenser 200 shown in FIG. 1A. It is further contemplated that reaction product effluent collecting assembly 70 include a storage assembly, preferably capable of segregating the reaction products from one another as well as segregating the unreacted gas stream from the reaction products.

As shown in FIGS. 10A, 10B, 11A, and 11B, first electrode 30b may comprise a substantially continuous wire which runs through the entirety of housing 20. Second electrode 40b may comprise a substantially conductive wire mesh on top of exterior surface 22 of housing 22 thereby substantially surrounding housing 20. Second electrode 40B is connected to a power source (not shown) via second lead 52a.

In operation, a gas stream as defined above enters housing 20 of gas stream conversion apparatus 10 via the gas stream introduction assembly 12. The gas stream is preferably methane, but it is also contemplated as containing an amount of oxygen, hydrogen, carbon dioxide, or combinations thereof. The gas is forced through housing 20 by the pressure generated by gas stream introduction and comes into contact assembly 12 with reaction zone 80a which is defined as the space between first electrode 30b and second electrode 40b. After entering reaction zone 80a, the gas stream encounters a discharge plasma (not shown) generated by first and second electrodes 30b and 40b, within reaction zone 80a by a power source (not shown) connected to the first and/or second electrodes 30b and 40b. The gas stream reacts with the discharge plasma generated within reaction zone 80a, thereby producing a reaction product. The reaction product will contain higher level hydrocarbons, some of which may contain an oxygen atom. Preferably, the reaction product will contain $C_2$ hydrocarbons, such as acetylene, ethane, and ethylene.

Figure 11A:
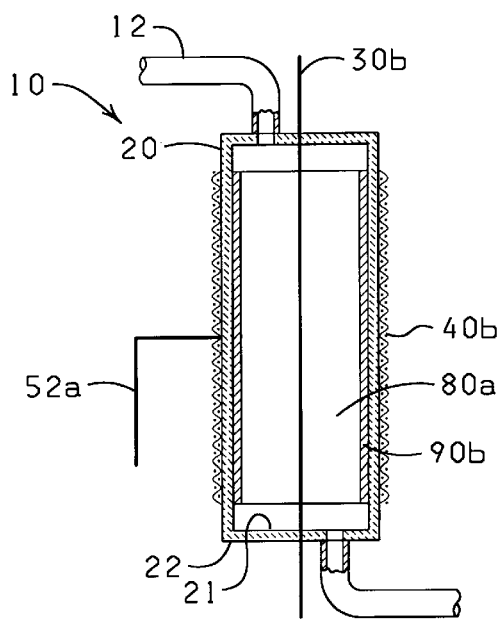
FIG. 11A of the drawings is a cross-sectional representation of the methane conversion apparatus of FIG. 10A, showing, in particular, a layer of material associated with the interior surface of the methane conversion apparatus housing.
Figure 11B:
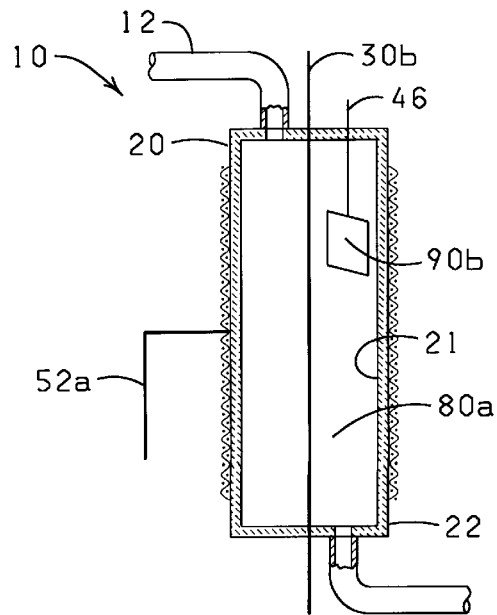
FIG. 11B of the drawings is a cross-sectional representation of the methane conversion apparatus of 10A, showing, in particular, a layer of material suspended within the housing.

If the gas conversion apparatus 10 contains a catalyst 90b, as shown in FIGS. 11A and 11B, the reaction of the gas stream containing hydrocarbons with the discharge plasma generated between first and second electrodes 30b and 40b will be affected in the manner described hereinabove. As shown in FIG. 11A, catalyst 90b may comprise a layer of material associated with the interior surface 21 of housing 20 or as shown in FIG. 11B, catalyst 90b may be suspended via suspension assembly 46. In any event, one of ordinary skill in the art can and will appreciate that catalyst 90b may be placed anywhere and by any means within housing 20 so long as catalyst 90b is capable of affecting the reaction of the gas stream containing hydrocarbons with the plasma discharge. In general, catalyst 90b will be capable of altering the conversion reaction and/or product selectivity. The reaction product and any remaining unreacted hydrocarbons will exit housing 20 as hereinabove described.

EXAMPLE ONE

In this example, the conversion apparatus has a wire and plate electrode configuration such as shown in FIG. 3A, wherein the tip of the wire electrode is 10 mm above the plate electrode. The reactor inner diameter is 7 mm. No heterogeneous catalyst is present on the plate electrode. The wire electrode is at +5 kV, the plate electrode is grounded. The reaction temperature is 923 K (650 C). Total flowrate of gases is 100 standard cubic centimeters per minute (SCCM) with the composition 12.5% oxygen, 50% methane, and 37.5% helium. Conversion of methane was 10.6% and conversion of oxygen was 17.2%. Combined $C_2$ selectivity (ethane, ethylene, acetylene) was 59.2%, for a total $C_2$ yield of 6.25% wherein $C_2$ yield represents the percentage of methane converted into $C_2$ species.

EXAMPLE TWO

In this example, the conversion apparatus has a wire and plate electrode configuration such as shown in FIG. 3A, wherein the tip of the wire electrode is 10 mm above the plate electrode. The inner diameter of the housing is 7 mm. No heterogeneous catalyst is present on the plate electrode. An AC electric field is applied between the electrodes, with a frequency of 60 Hz and an amplitude of 5 kV rms. Reaction temperature is 923 K. The total flowrate of gases is 50 SCCM with the composition being 12.5% oxygen, 50% methane, and 37.5% helium. Conversion of methane was 58%. Combined $C_2$ selectivity was 34%, for a total $C_2$ yield of 20%.

EXAMPLE THREE

In this example, the conversion apparatus has a wire and plate electrode configuration such as shown in FIG. 4A, wherein the tip of the wire electrode is 10 mm above the plate electrode and about 2 mm above the top of a catalyst bed. The inner diameter of the housing is 7 mm. The catalyst bed is 0.1 g of $Sr/La_2O3$. The wire electrode is at +5 kV, the plate electrode is grounded. The reaction temperature is 823 K. The total flowrate of gases is 100 SCCM with the composition being 20% oxygen, 50% methane, and 30% helium. The combined $C_2$ selectivity was 40%, for a combined $C_2$ yield of 11%. The acetylene to ethane ratio in the product was 0.73.

EXAMPLE FOUR

In this example, the conversion apparatus has a wire and plate electrode configuration such as shown in FIG. 4A, wherein the tip of the wire electrode is 10 mm above the plate electrode and about 2 mm above the top of a catalyst bed. The inner diameter of the housing is 7 mm. The catalyst bed is 0.1 g of NaOH-treated Y zeolite. The wire electrode is at +5 kV and the input power is approximately 7 watts. The plate electrode is grounded. The reaction temperature is 373 K. The total flowrate of gases is 100 SCCM with the composition being 12.5% oxygen, 50% methane and 37.5% helium. Conversion of methane was 14.8%. The combined $C_2$ selectivity was 42%, for a combined $C_2$ yield of 6.3%. The acetylene to ethane ratio in the product was 20:1, and the CO to $CO_2$ ratio in the product was about 60:1.

EXAMPLE FIVE

In this example, the conversion apparatus is set up the same as in Example Four except that the wire electrode is at +6 kV and the input power is 6.5 watts, with a gas flowrate of 10 sccm and an inlet composition of methane at 20%, hydrogen at 30%, oxygen at 2% and the remaining material being helium. In this example, the methane conversion is 63.5%. The largest product is acetylene with a selectivity of about 48%. The $C_2$ yield is 32.6%. A small amount of carbon monoxide is produced from the oxygen.

EXAMPLE SIX

Figure 10A:
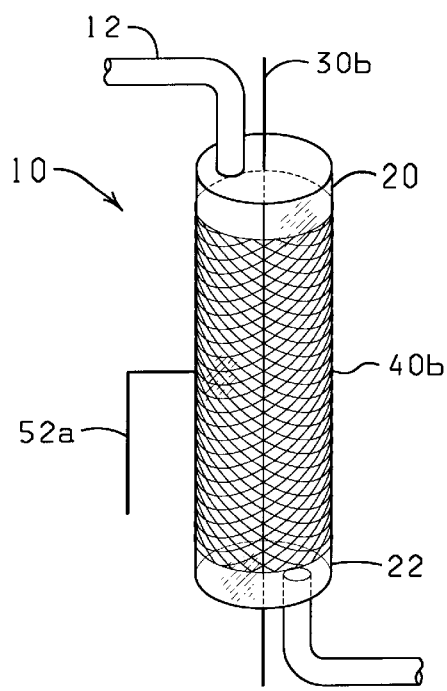
FIG. 10A of the drawings is a pictorial representation of a methane conversion apparatus embodying an embodiment of the present invention showing the first electrode as substantially continuous throughout the interior of the housing and the second electrode comprising a conducting material substantially surrounding the outer surface of the housing.
Figure 10B:
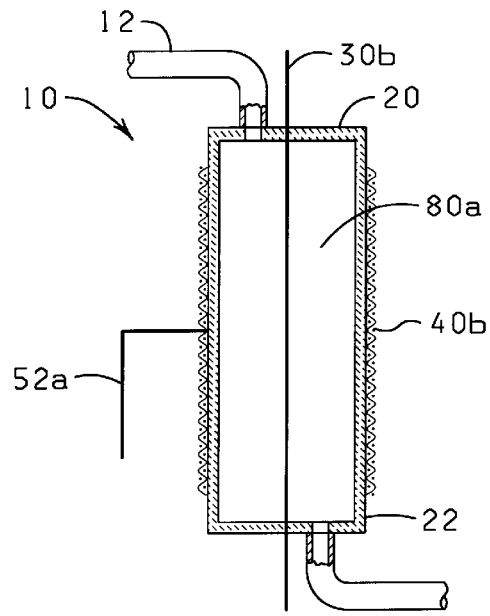
FIG. 10B of the drawings is a cross-sectional representation of the methane conversion apparatus of FIG. 10A, showing, in particular, the substantially continuous first electrode and the second electrode as a conducting material substantially surrounding the outer surface of the housing.

In this example, the conversion apparatus has an internal wire electrode and an external wire electrode consisting of metal wire mesh affixed to the outside of the non-conducting, dielectric, reactor tube which is made out of quartz, as shown in FIG. 10A.

The length of the wire mesh cloth along the axis of the tube is 8 cm. The inner diameter of the tube is 7 mm. The total flowrate of gas to the vessel is 10 sccm with the composition of methane and carbon dioxide each at 50 percent. An AC voltage of 5 kV at a frequency of 390 Hz is applied. The power used is 22 watts and the methane conversion is 28.8 percent. The primary product is ethane, which has a selectivity of 26.6% for a yield of 6.7%. The carbon dioxide conversion is 19.0%, primarily to carbon monoxide. Hydrogen is produced but was not quantified.

FIGS. 5–9 show another series of embodiments of the present invention wherein the gas stream conversion apparatus comprises a plurality of electrodes and spacing plates disposed in a parallel orientation. One such embodiment is shown in cross-sectional view in FIG. 5 and in an exploded perspective view in FIG. 5A and is referenced to therein as gas stream conversion apparatus 310. Apparatus 310 comprises a first outer plate 320, having an interior surface 321 and an exterior surface 322, a second outer plate 325, having an interior surface 326 and an exterior surface 327, a first electrode 330 having a first surface 331, a second surface 332, and a first lead 333, wherein first electrode first surface 331 is substantially adjacent first outer plate interior surface 321, a second electrode 340 having a first surface 341, a second surface 342, a second lead 343, a plurality of passageways 344a and 344b, a first outer edge 345, a second outer edge 346, a first outer end 347, and a second outer end 348, a first spacing assembly 350 having a space 353 and an upper surface 351, a second spacing assembly 360 having a first surface 361, a second surface 362, and first and second passageways 363 and 364, respectively, extending from surface 361 to 362 through second spacing assembly 360, a gas stream introduction assembly 370, and a collecting assembly 380.

The first and second outer plates 320, 325 may be fabricated from a non-conducting material such as glass or quartz, although one of ordinary skill in the art would understand that first and second outer plates 320, 325 may be fabricated from any suitable non-conductive material such as glass or plastic. It will also be understood that first and second outer plates 320, 325 may be fabricated from a conductive material if first outer plate interior surface 321 and second outer plate interior surface 326 are coated with a non-conductive material or laminated with a non-conductive material. Gas stream conversion apparatus 310 may also include a temperature regulator assembly (not shown) operably associated with first and second outer plates 320, 325 so as to regulate the temperature between first and second outer plates 320, 325. It will be understood by one of ordinary skill in the art, that first and second outer plates 320, 325 form a housing when integrally associated with one another by securing assembly 900.

In one embodiment, securing assembly 900 comprises screws integrally placed around the periphery so as to hold components 330, 340, 350, and 360 in a "sandwich" between first and second outer plates 320, 325. It will, however, be appreciated by one of ordinary skill in the art that any fastening device capable of attaching first and second outer plates 320, 325 together in accordance with the present invention is acceptable for use. For example, securing assembly 900 may comprise a plurality of fasteners, or combination of fasteners, such as screws or binders, which are functional as clamps, integrally associating first and second outer plates 320, 325 into the housing. It will also be understood by one of ordinary skill in the art that in another embodiment the entire apparatus 310 may be disposed within a second housing which fully encloses apparatus 310.

Second electrode first surface 341 is substantially adjacent second spacing assembly second surface 362. First and second electrodes 330, 340, first and second leads 333, 343 attached to the periphery of first and second electrodes 330, 340 and a power source (not shown) operably attached to first and second leads 333, 343 together comprise a plasma discharge assembly.

Figure 5:
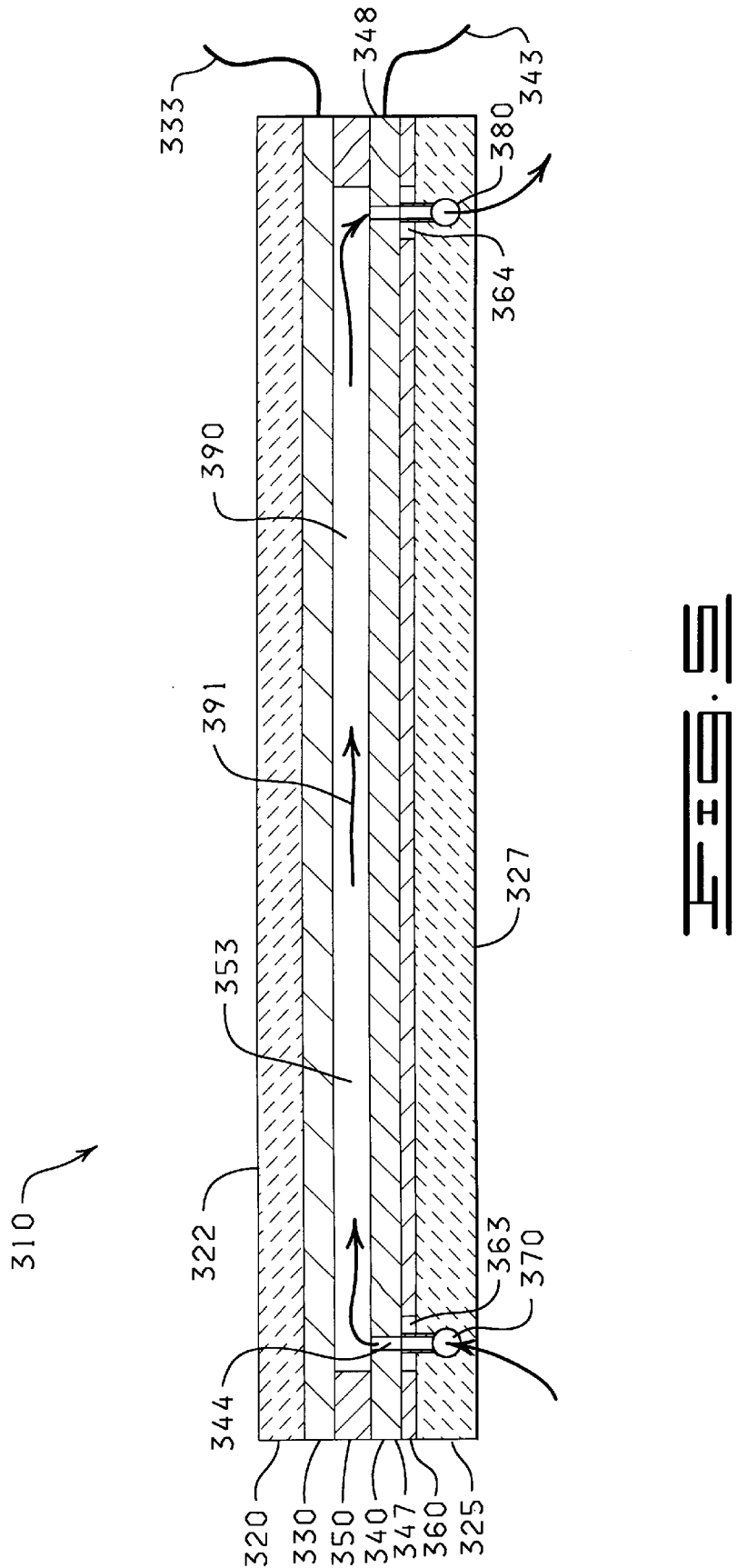
FIG. 5 is a side sectional view of an apparatus constructed in accordance with the present invention.
Figure 5A:
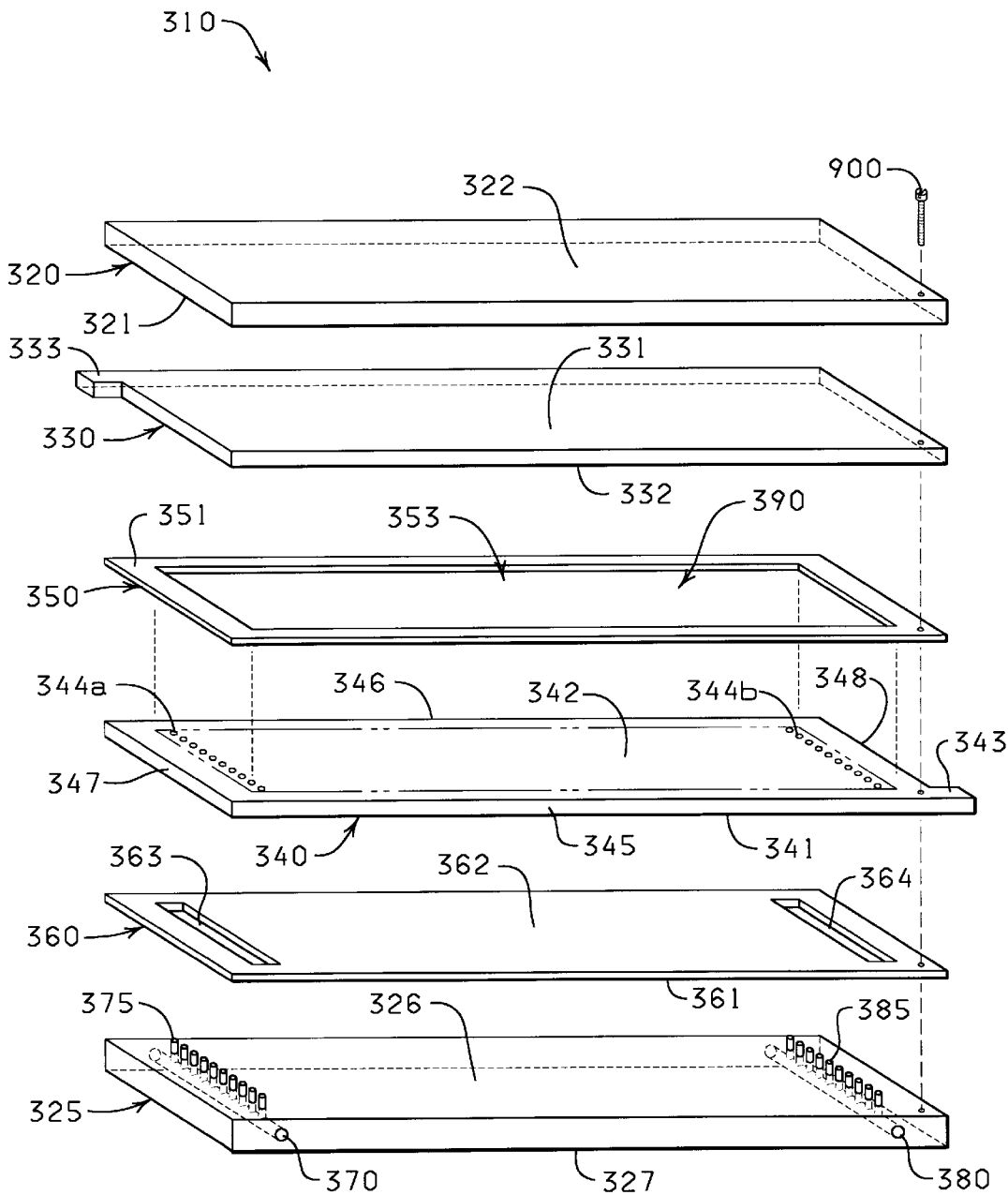
FIG. 5A of the drawings is an exploded pictorial representation of the methane conversion apparatus of FIG. 5, showing, in particular, the first and second electrodes comprising plate electrodes and a non-conducting spacer.

As shown in FIGS. 5 and 5A, in a preferred version of the invention, first electrode first surface 331 is substantially adjacent first outer plate interior surface 321. First electrode second surface 332 faces and is substantially adjacent second electrode second surface 342, with first spacing assembly 350 being operatively disposed between first electrode second surface 332 and second electrode second surface 342. Second electrode first surface 341 faces and is substantially adjacent second spacing assembly second surface 362. Second spacing assembly first surface 361 faces and is substantially adjacent second outer plate interior surface 326. Also, as can be appreciated from FIG. 9, gas stream conversion apparatus 310 can be positioned at an angle 750 (for example, 90 to 45 degrees) relative to a horizontal support surface, such as horizontal support surface 800 to facilitate the drainage of condensed reaction products. Of course, one of skill in the art would appreciate that gas stream conversion apparatus 310 may be positioned at any angle relative to a horizontal surface, provided such angle encourages the drainage of a condensed reaction product from the gas stream conversion apparatus 310.

Gas stream conversion apparatus 310 is also used in the conversion of a gas stream containing hydrocarbons (referred to hereinafter as the "gas stream") to molecules having at least one carbon atom and preferably to $C_2$ (two carbon) hydrocarbons such as acetylene, ethane or ethylene as explained with regard to gas stream conversion apparatus 10 of FIG. 1A. The gas stream will generally contain primarily methane in the form of natural gas. Of course, it will be appreciated that the characteristics with regard to the gas stream will be identical to those described above with regard to the gas stream conversion apparatus 10-i.e. that it may also contain amounts of oxygen, hydrogen, or carbon dioxide.

As noted above, gas stream conversion apparatus 310 further includes a gas introduction assembly 370 for introducing the gas stream into a reaction space 390 between first and second electrodes 330, 340. Gas introduction assembly 370 may be a conduit, pipe, tank, or pump capable of introducing the gas stream between first and second electrodes 330, 340 at a constant pressure with the resultant effect that the pressure between first and second electrodes 330, 340 forces any reaction product effluent produced within the space 395 to exit the gas stream conversion apparatus 310 via the collecting assembly 380. Gas introduction assembly 370 may also include a regulator or series of pumps and regulators capable of introducing the gas stream into gas stream conversion apparatus 310 and may further include introduction assemblies having the ability to introduce and regulate the flow of distinct gases or gas mixtures into gas stream conversion apparatus 310. Such assemblies are commercially available and are known to those of ordinary skill in the art.

When a gas stream is introduced by assembly 370, the gas flows through passageway 363 and channels 344a into space 390 in a direction 391. Effluent continues to flow in direction 391 until it exits through channels 344b, through passageway 364, and exits the gas stream conversion apparatus 310 at assembly 380.

First electrode 330 and second electrode 340 are preferably fabricated from one or more materials capable of generating an electric field therebetween when an electric charge is applied to first and second electrodes 330, 340. In one version, first and second electrodes 330, 340 are fabricated from stainless steel and may be generally shaped, as shown in FIGS. 5 and 5A, as plates generally parallel to one another, wherein first electrode 330 has a length approximately equal to that of second electrode 340. The first electrode 330 may be conductive along its entire length, or only a centrally-located portion of the electrode 330 which has a surface area one-half to one-third of the surface area of the second electrode 340 may be conductive, as discussed in more detail below.

First and second electrodes 330, 340 are spaced apart a predetermined distance by first spacing assembly 350 which has a generally rectangular passageway 353 extending therethrough wherein rectangular passageway 353 generally defines a reaction zone 390. First spacing assembly 350 is fabricated from a dielectric material and in one preferred embodiment, the dielectric material is glass. It is also contemplated that first spacing assembly 350 be fabricated from different dielectric materials. Further, first spacing assembly 350 may comprise an insulating material such as rubber. Furthermore, first electrode 330 and/or second electrode 340 may have a dielectric material operably associated therewith, such as glass, in addition to first spacing assembly 350.

In one embodiment, first lead 333 may be connected to a power supply thereby directing a voltage to first electrode 330, while second lead 343 may ground second electrode 340 to a voltage of zero or opposite polarity when AC is used, wherein the plasma discharge assembly induces the formation of a plasma discharge within the reaction zone 390 between first and second electrodes 330, 340. The electric field may be created by either a high voltage DC power supply or an AC power supply (which may include various waveform shapes such as sinusoidal, square, pulsed, modified square and rectified) with a high voltage transformer. When DC power is applied, second electrode 340 is grounded and first electrode 330 is at either a positive potential (referred to as positive corona) or negative potential (referred to as negative corona). It is contemplated that the electric field will take the form of a plasma discharge as hereinabove described in detail with regard to the gas stream conversion apparatus 10 of FIG. 1A.

First and second electrodes 330, 340 are positioned relative to one another such that when connected to an energy source, such as a DC energy source, a plasma discharge is created therebetween. Although the plasma discharge assembly has been disclosed as including a DC energy source, it will be understood that any energy source capable of producing a plasma discharge between first and second electrodes 330, 340, is contemplated for use. Examples of such other energy sources would be AC, RF, or MV energy sources.

Although first and second electrodes 330, 340 have been described as being fabricated from stainless steel, it will be understood by one of ordinary skill in the art that first and second electrodes 330, 340 may be fabricated from any material capable of generating an electric field therebetween when an electric current is applied to at least one of the first and second electrodes 330, 340. Furthermore, first electrode 330 may be fabricated from a different material than second electrode 340. Reaction zone 390 is the space between first and second electrodes 330 and 340, wherein the gas stream introduced by gas introduction assembly 370 reacts with the electric field generated by first and second electrodes 330, 340. As noted above, second electrode 340 includes a plurality of first passageways 344a extending therethrough for allowing the gas stream to freely pass through second electrode 340 to reaction zone 390. Similarly, second electrode 340 also includes a plurality of second passageways 344b extending therethrough for allowing the reaction product effluent to pass from reaction zone 390 through second electrode 340 and subsequently through second spacing assembly second passageway 364 toward reaction product effluent collecting assembly 380, as described above.

Figure 5B:
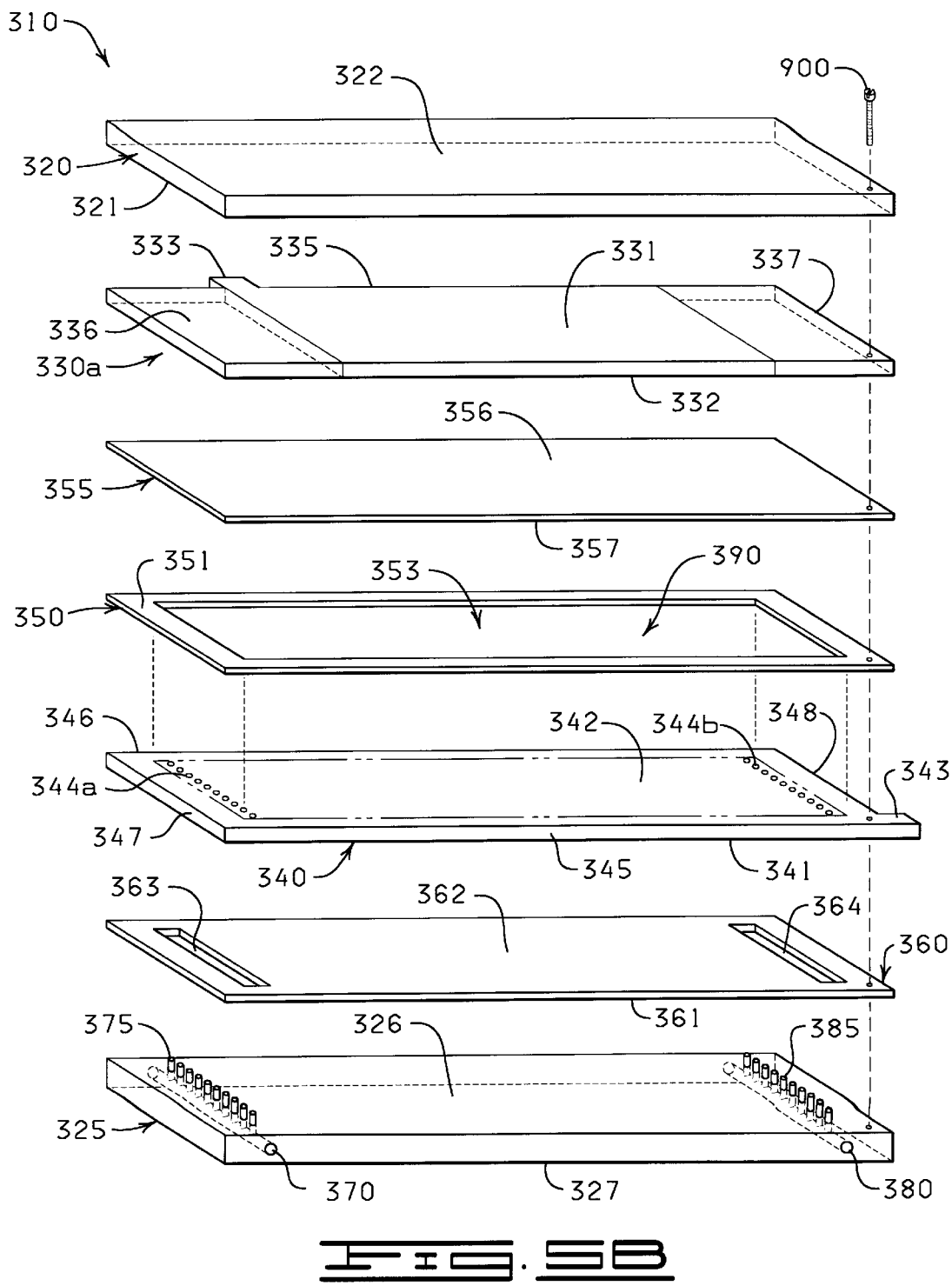
FIG. 5B of the drawings is an exploded pictorial representation of another version of the methane conversion apparatus of FIG. 5 further comprising a dielectric material between the non-conducting spacer material and the first and second electrodes.

An alternative embodiment of the apparatus 310, shown in FIG. 5B, comprises a third spacer 355 having a first surface 356 and a second surface 357. The first surface 356 is disposed adjacent surface 332 of electrode 330 and the second surface 357 is disposed facing surface 342 of electrode 340 and adjacent upper surfaces 351 of spacer 350 thereby forming a shield between the surface 332 of electrode 330 and the reaction zone 390. Third spacer 355 may be fabricated in the same manner as spacers 350 and 360 discussed above.

As noted previously, first electrode 330 may have a conducting surface area equal to or of a different size than that of the conducting surface of second electrode 340. FIG. 5B shows such a case wherein an electrode assembly 330a comprises a conducting portion 335 having a surface area less than that of electrode 340. The electrode assembly 330a further comprises a first extension 336 and a second extension 337 which extend from each end of the conducting portion of electrode 330a for enabling the electrode assembly 330a to be positioned suitably within the apparatus 310.

Figure 5C:
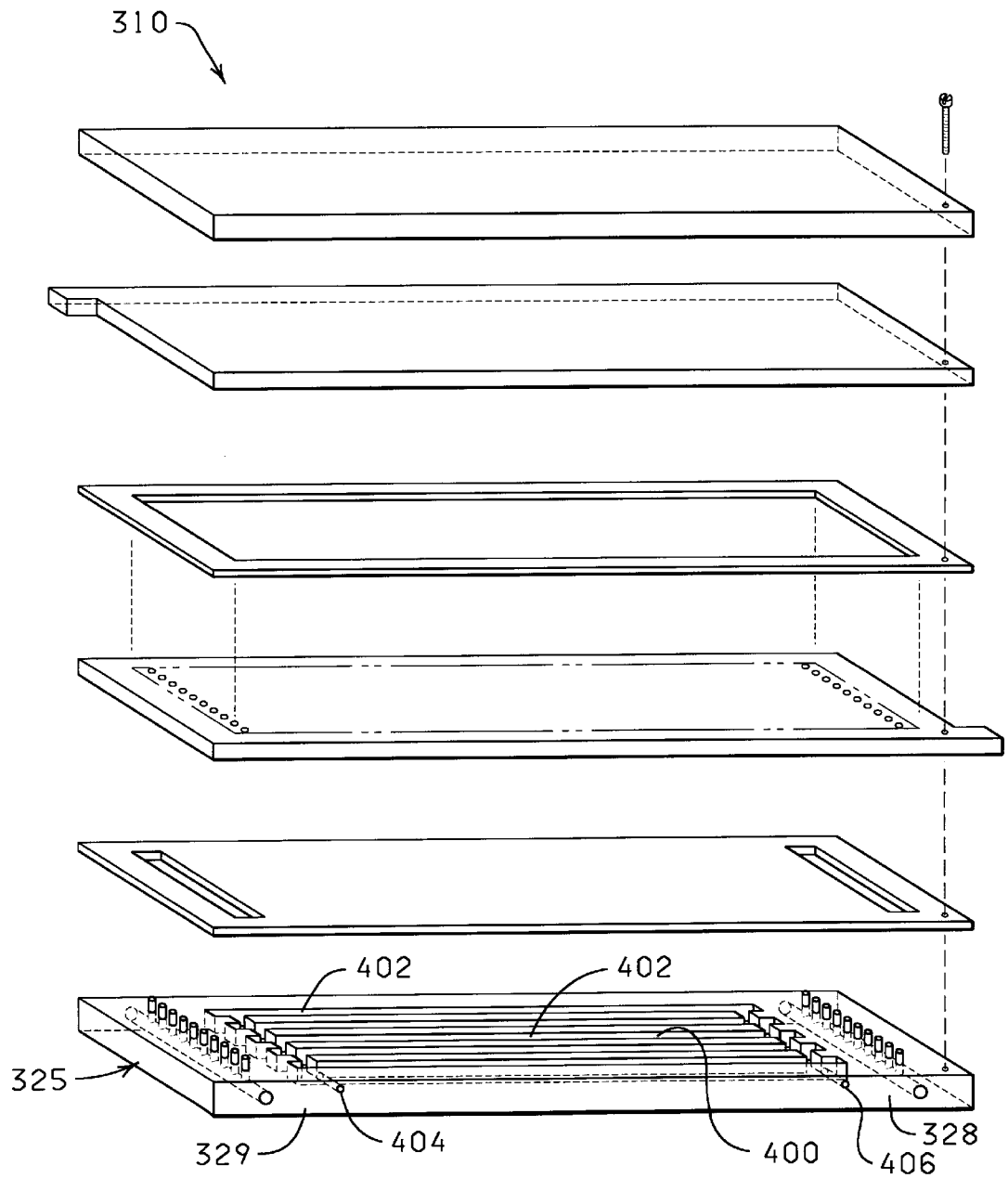
FIG. 5C of the drawings is an exploded pictorial representation of the methane conversion apparatus of FIG. 5, further comprising a condensing means.

In another embodiment of the invention as shown in FIG. 5C, gas stream conversion apparatus 310 is exactly the same as apparatus 310 in FIG. 5A except it further includes a condensing assembly 400 operably associated with second outer plate 325. Condensing assembly 400 includes a plurality of condensing channels 402, a condensing assembly inlet 404, a condensing assembly outlet 406, and a condensing fluid introduction assembly (not shown) for introducing a condensing fluid into the condensing assembly. Condensing channels 402 are operably associated with second plate 325 as shown in FIG. 5C. Condensing channels 402 comprise channels extending into second outer plate 325 from second plate interior surface a predetermined distance (not shown). The predetermined distance will preferably be a distance capable of allowing the passage of an effective amount of a condensing liquid through condensing channels 402, thereby enabling the regulation of the temperature of gas stream conversion assembly 310. Condensing channels 402 are operably attached to a condensing fluid recycling assembly (not shown) via condensing assembly inlet 404 and condensing assembly outlet 406. The condensing fluid recycling assembly includes a storage and/or regulation apparatus capable of introducing a condensing fluid, such as water, into condensing channels 402 at a predetermined flow rate in a manner well known to those of ordinary skill in the art. A condensing fluid is introduced into condensing channels 402 via condensing assembly inlet 404. Condensing assembly inlet 404 is connected to condensing fluid recycling assembly at second outer plate second edge 329, and condensing assembly inlet 404 thereafter extends through second outer plate 325 and operably connects with condensing channels 402. Condensing assembly outlet 406 is connected to the condensing fluid recycling assembly (not shown) at second outer plate first edge 328, and condensing assembly outlet 406 thereafter extends through second outer plate 325 and operably connects with condensing channels 402. One of skill in the art will appreciate that the condensing assembly 400 as shown in FIG. 5C is but one embodiment of such a condensing means and that any unit capable of allowing the sufficient flow of condensing liquid enabling the lowering of the temperature of gas stream conversion apparatus in order to allow the condensation of a reaction product would be suitable.

Figure 6:
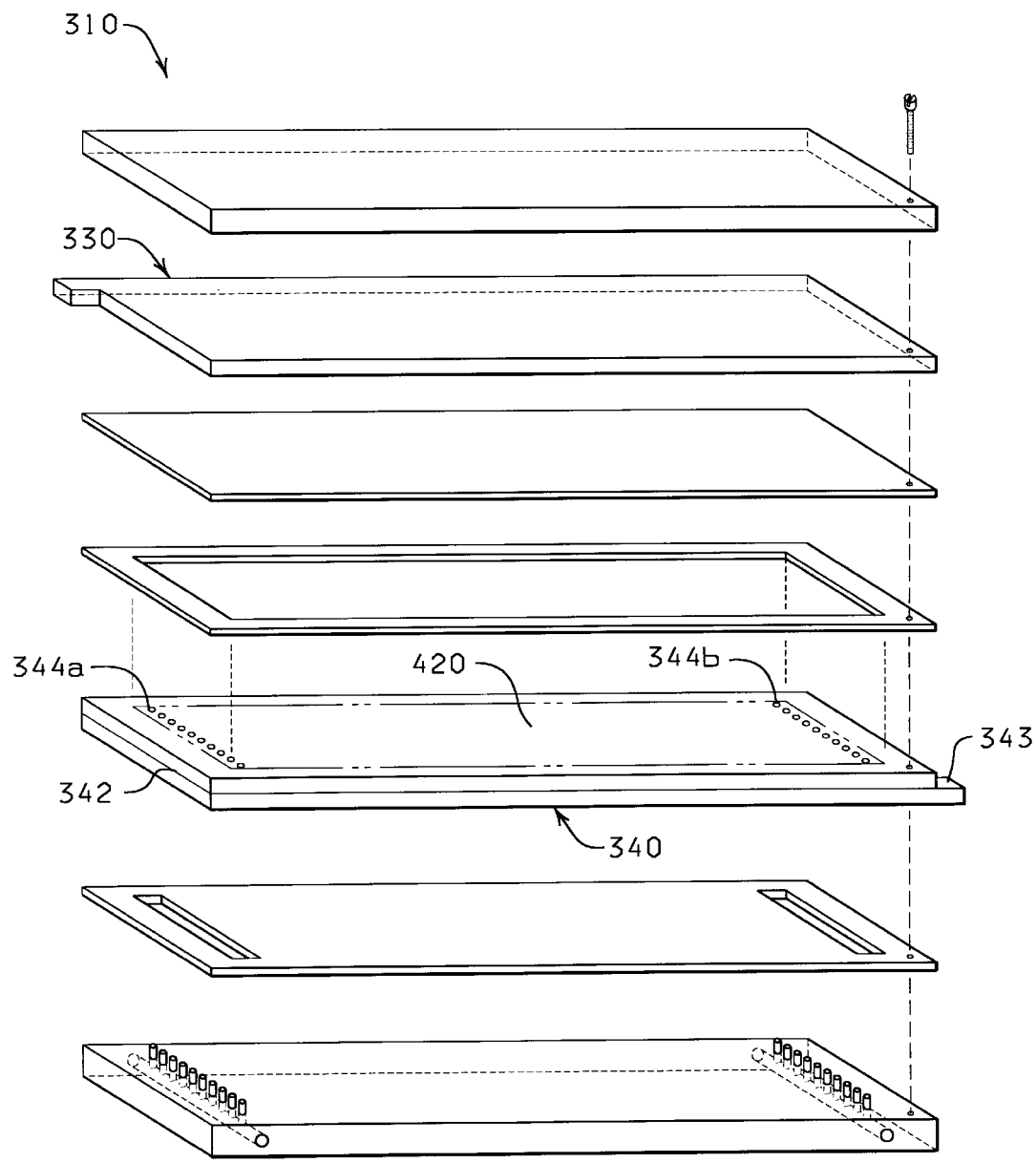
FIG. 6 of the drawings is an exploded pictorial representation of the methane conversion apparatus of FIG. 5B, showing, in particular, a layer of catalytic material operably connected to the second electrode.

FIG. 6 shows a gas stream conversion apparatus 310 substantially the same as that shown in FIG. 5B except the gas stream conversion apparatus 310 in FIG. 6 comprises an amount of a catalytic material 420 disposed upon, or otherwise associated with at least a portion of second electrode 340, and more preferably, the catalyst 420 is disposed upon the entire second electrode second surface 342. Although catalyst 420 is disposed on, or otherwise associated with, second electrode 340, catalyst 420 may alternatively be disposed on first electrode 330. Generally, catalysts used in OCM reactions may be classified as either reducible or irreducible metal oxides. Methane and oxygen may be fed alternately over reducible oxides and a redox mechanism for the reaction has been suggested for the production of $C_2$ products, wherein the metal oxide acts as both the reducing and oxidizing agent. Irreducible metal oxides, such as catalysts with rare-earth oxides, act as catalysts which are favorable for OCM. However, over both reducible and irreducible catalyst oxides, OCM in the absence of a corona discharge plasma still requires high reaction temperatures. A gas stream conversion apparatus 310 having a catalyst 420 on second electrode 340 may also encourage the selectivity of $C_2$ products at low temperatures. Where catalyst 420 covers the entire surface 342 of electrode 340, passageways 344a and 344b extend through the catalyst 420 for allowing passage of the gas stream into the reaction zone 390.

Catalyst 420, as described above, may be a single metal oxide or a multiple metal oxide. Single metal oxides contemplated for use include CaO, PbO, $Sm_2O_3$, and $La_2O_3$. Multiple metal oxides contemplated for use include Li/MgO, $Sr/La_2O_3$, $Sm_2O_3$, NaOH/CaO, $Na_2O/Pr_2O_3$, Ca/Ni/K oxide, $La_2O_3$, $Bi_2O_3$—$K_2CO_3$—$Al_2O_3$. Furthermore, catalyst 420 may include perovskites such as $LaMnO_3$, $LaAlO_3$, $SrTiO_3$, $CrLa_{1-x}Sr_xO_3$, and $BaPb_{1-x}Bi_xO_3$. Finally, it is contemplated that catalyst 420 be a zeolite, such as mordenite, faujasite, Y or X zeolite, and ZSM5, all of which may also be altered by various treatments, as described hereinabove. Although catalyst 420 has been disclosed as encompassing specific examples of single and multiple metal oxides, perovskites, and zeolites, it will be understood by a person of ordinary skill in the art that any material capable of modifying the reaction of the gas stream within the reaction zone 390, is contemplated for use as catalyst 420.

In an alternative of the invention, the apparatus 310, as shown in FIGS. 7A and 7B, second electrode 340 may contain one or more of channels 430, identified herein as channels 430a–430e, which extend lengthwise as grooves within electrode 340 wherein channels 430 face electrode 330. As shown in FIG. 7B, each channel 430 has a width 432 and a length 434 (FIG. 7A). Channel 430a is positioned a distance 436 from second electrode first outer edge 345, and channel 430e is positioned a distance 436 from second outer edge 346. Although five channels are shown in FIGS. 7A and 7B, one of ordinary skill in the art will understand that the number of channels in electrode 340 may be fewer than five or more than five, as long as the channels function in accordance with the present invention. Furthermore, a spacing member, such as spacing member 438, is operably disposed in between each pair of channels. Each spacing member 438 has a width 440. It will be understood by one of ordinary skill in the art that the width 432 or depth 433 of each channel 430 may be made lesser or greater, for optimizing the function and performance of the channels 430 in the electrode. It will also be understood that the orientation of the channels 430 may be adjusted so as to optimize their performance, for example, portions of the channel may extend at an angle to the main orientation of the channel.

Channels 430 may contain one or more materials capable of adsorbing and/or absorbing an adsorbable and/or absorbable reaction product produced by the reaction of the gas stream with the plasma discharge. If the reaction product is an absorbable reaction product, the material within channels 430 may be a liquid capable of absorbing the absorbable reaction product, such as a solution of an effective amount of a silver salt. If the reaction product is an adsorbable reaction product, the material within channels 430 may be a solid capable of adsorbing the adsorbable reaction product, such as an effective amount of a zeolite. It will be understood to those of ordinary skill in the art, that the choice of adsorbable or absorbable material will depend upon the particular characteristics of the reaction product sought to be collected. For example, if the reaction product sought to be isolated is ethylene, channels 430 may be filled with an effective amount of a silver salt solution.

Alternatively, the channels 430 may be coated or filled with a catalytic material as described above in regard to catalyst 420.

In an alternate embodiment of the invention as shown in FIG. 8, gas stream conversion apparatus 310 is substantially the same as that shown in FIG. 5B, except that second electrode 340 is comprised of a substantially porous material, second spacing assembly 360 has a generally rectangular passageway 365 extending therethrough positioned between passageways 363 and 364, and second outer plate 325 has a drain 382 operably associated therein for the draining of a liquid reaction product produced in reaction zone 390. Drain 382 operably extends from second outer plate interior surface 326 to an external opening in the second outer plate 325. In operation, a liquid reaction product produced by the reaction of a gas stream with a plasma discharge produced by first and second electrodes 330, 340 within reaction zone 390 filters through the porous openings in second electrode 340, and subsequently through generally rectangular passageway 365 of second spacing assembly 360 towards drain 382. Drain 382 thereafter directs the liquid reaction product to a collection assembly (not shown) operably attached to the external opening of drain 382. Therefore, as can be appreciated from FIG. 8, a gas stream conversion apparatus 310 having the ability to withdraw a liquid reaction product through a porous second electrode 340 is provided.

In operation of any of the embodiments described above, a gas stream as defined above, preferably containing methane, is introduced into the reaction zone 390 between first and second electrodes 330, 340 of gas stream conversion apparatus 310 via the gas stream introduction assembly 370. The gas stream may also generally contain an amount of oxygen. The gas is forced through gas stream passageways 375 by the pressure generated by gas stream introduction assembly 370. The gas stream flows through gas stream passageways 375, which extend into and through second spacing assembly 360 via second spacing assembly first passageway 363. Gas stream passageways 375 thereby operably connect with second electrode first passageways 344a. After passing through second electrode first passageways 344a, the gas stream enters reaction zone 390, where it encounters a corona discharge plasma (not shown) generated by first and second electrodes 330, 340 within reaction zone 390 by a power source (not shown) connected to the first and/or second electrodes 330, 340. The gas stream reacts with the corona discharge plasma generated within reaction zone 390, thereby producing a reaction product wherein the reaction product may be a gas, a liquid, or a combination of a gas or liquid. Furthermore, if second electrode 340 contains channels 430 (as shown in FIGS. 7A and 7B), the reaction product may be adsorbed or absorbed by a material within channels 430, as previously described hereinabove. The reaction product will contain higher level hydrocarbons, or some products which may contain an oxygen atom.

If the gas stream conversion apparatus 310 contains a catalyst 420 disposed on or in an electrode, such as catalyst 420 disposed on electrode 340 in FIG. 6, the reaction of the gas stream containing hydrocarbons with the corona discharge plasma generated between first and second electrodes 330, 340 will be affected in the manner described hereinabove. Namely, the catalyst 420 will alter the conversion reaction and/or product selectivity.

The reaction product, any remaining unreacted hydrocarbons, and/or any non-adsorbed or non-absorbed reaction products, from the gas stream, will thereafter be forced out of reaction zone 390 by the pressure created by gas stream introduction assembly 370. The reaction product, remaining unreacted hydrocarbons, and/or any non-absorbed or non-adsorbed reaction product, are forced through a plurality of second passageways 344b extending through a portion of second electrode 340, and caused to exit gas stream conversion apparatus 310 via exit passageways 385. Exit passageways 385 operably connect to second electrode second passageways 344b at second electrode first surface 341 and extend downwardly through second spacing assembly 360 via second spacing assembly second passageway 364. After extending through second spacing assembly 360, exit passageways 385 operably connect to collecting assembly 380. The reaction product may be a gas, a liquid or a combination of a gas and liquid. The reaction product will generally comprise a liquid if the temperature within gas stream conversion apparatus 310 is below that of the condensation point of the reaction product. If gas stream conversion apparatus 310 contains condensing assembly 400 (as shown in FIG. 5C), the reaction product will have condensed within the gas stream conversion apparatus 310 and the reaction product effluent entering the collecting assembly 380 will be a liquid or a combination of a liquid and a gas. Therefore, reaction product effluent collecting assembly 380 may comprise an outlet tube, pipe or conduit capable of allowing the reaction product to exit the gas stream conversion apparatus 310. Reaction product effluent collecting assembly 380 may also be connected to an analysis assembly (not shown) for the quantitative analysis of the reaction product. It is further contemplated that reaction product effluent collecting assembly 380 includes a storage assembly, preferably capable of segregating the reaction products from one another as well as segregating the unreacted gas stream from the reaction products. The unreacted gas stream components may be recycled back into the gas introduction assembly 370 by means not shown for further processing.

It is also contemplated herein that any of the aspects of the various embodiments described in FIGS. 5–9, such as spacing elements, electrode channels, adsorbing, absorbing or catalytic materials, condensing means, or electrode construction, may be combined in various ways to construct other versions of the apparatus which function in accordance with the invention as contemplated herein.

EXAMPLE SEVEN

In this example, the conversion apparatus has a plate and plate electrode configuration such as shown in FIG. 5, wherein the spacing between the plate electrodes is 0.5 inches. No heterogeneous catalyst is present on the plate electrode. The inner diameter of the housing is 7 mm. An AC electric field is applied between the electrodes, with a frequency of 150 Hz and an amplitude of 6.25 kV rms. Gases are fed at room temperature. The total flowrate of gases is 100 SCCM with the composition being 7.5% oxygen, 30% methane and 62.5% helium. Conversion of the methane was 25%. Combined ethane and ethylene selectivity was 52%, for a total $C_2$ yield of 13%.

EXAMPLE EIGHT

In this example, the conversion apparatus has a parallel plate reactor configuration with a glass dielectric, such as shown in FIG. 5. The methane to oxygen ratio was 3:1, with no other feed components. The flowrate of the gases was 200 cc/min. An AC sinusoidal waveform at 100 Hz with a voltage of 5 kV was applied. A methane conversion of 24.81% is achieved with gas product selectivities of 15.07% $CO_2$, 4.88% ethane, and 18.12% CO. Liquid selectivities are 2.33% formaldehyde, 22.72% methanol, 8.11% methyl formate, 0.02% ethanol and 21.94% formic acid. Liquid is collected as a concentrated (50+% organic) aqueous solution.

EXAMPLE NINE

In this example, the conversion apparatus has a parallel plate reactor with a glass dielectric, such as shown in FIG. 5. The methane to oxygen ratio was 3:1, with 40 cc/min $CO_2$, a total flow rate of 200 cc/min, using an AC sinusoidal waveform at 100 Hz with a voltage of 9.75 kV. A methane conversion of 24.22% is achieved with gas product selectivities of 0% $CO_2$ ($CO_2$ production is suppressed by $CO_2$ in the feed), 4.59% ethane, 37.26% CO. Liquid selectivities are 11.76% formaldehyde, 11.10% methanol, 15.54% methyl formate and 18.65% formic acid. Liquid is collected as a concentrated (50+% organic) aqueous solution.

EXAMPLE TEN

In this example, the conversion apparatus has a parallel plate reactor with a glass dielectric, such as shown in FIG. 5. A methane only feed is fed at a total rate of 10 cc/min. An AC sinusoidal waveform is used at 155 Hz with a voltage of 5.4 kV. A methane conversion of 55% is achieved with gas product selectivity of 22% ethane. Propane, butane and C5+ are also present in significant amounts but for which there were not specific calibrations. No carbon buildup was observed and hydrogen was also produced.

Thus, it should be apparent that there has been provided in accordance with the present invention an apparatus and method for converting a gas stream containing hydrocarbons to a reaction product containing at least one carbon atom that fully satisfies the objectives and advantages set forth above. Although the invention has been described in conjunction with specific embodiments thereof, it is evident that many alternatives, modifications and variations will be apparent to those skilled in the art. Accordingly, it is intended to embrace such alternatives, modifications and variations that fall within the spirit and broad scope of the appended claims.

What is claimed is:

1. An apparatus for converting a gas stream containing hydrocarbons to a reaction product containing effluent molecules having at least one carbon atom, comprising:
    a housing, having at least one interior surface and at least one exterior surface;
    a first electrode and a second electrode, wherein the first electrode and the second electrode are selectively movable in relation to each other and positioned within the housing so as to be spatially disposed a predetermined distance from each other;

means for producing a plasma discharge between the first electrode and the second electrode;

means for passing the gas stream containing hydrocarbons between the first electrode and the second electrode;

means for collecting the reaction product effluent produced by the reaction of the gas stream containing hydrocarbons with the plasma discharge between the first and second electrodes; and means for absorbing an absorbable reaction product produced by the reaction of the gas stream containing hydrocarbons with the plasma discharge.

2. The apparatus of claim 1, wherein the absorbing means is a liquid capable of absorbing the absorbable reaction product.

3. The apparatus of claim 2, wherein the liquid is a solution of an effective amount of a silver salt.

4. The apparatus of claim 1, wherein the adsorbing means is a solid capable of adsorbing the adsorbable reaction product.

5. The apparatus of claim 4, wherein the solid is an effective amount of an adsorbant.

6. The apparatus of claim 5, wherein the adsorbant is a zeolite.

7. A method for converting a gas stream containing hydrocarbons to a reaction product effluent containing molecules having at least one carbon atom, comprising the steps of:

providing an apparatus, wherein the apparatus comprises,
a housing having at least one interior surface and at least one exterior surface,
a first electrode and a second electrode, wherein the first and second electrodes are selectively movable in relation to each other and positioned within the housing so as to be spatially disposed a predetermined distance from each other,
means for producing a plasma discharge between the first and second electrodes,
means for passing the gas stream containing hydrocarbons between the first and second electrodes; and
means for collecting a reaction product effluent from the housing;

producing a plasma discharge between the first and second electrodes;

introducing a gas stream containing hydrocarbons into the housing, wherein the gas stream is passed into the plasma discharge causing the hydrocarbons within the gas stream to be converted into reacted hydrocarbons having at least two carbon atoms;

absorbing an absorbable reaction product produced by the reaction of the gas stream containing hydrocarbons with the plasma discharge; and collecting the reacted hydrocarbons as an effluent from the housing.

8. The method of claim 7, further comprising absorbing an absorbable reaction product, by using a liquid capable of absorbing the absorbable reaction product.

9. The method of claim 7, further comprising absorbing an absorbable reaction product, by using an effective amount of a silver salt.

10. The method of claim 7, wherein in the step of providing a means for adsorbing an adsorbable reaction product, the adsorbing means is a solid capable of adsorbing the adsorbable reaction product.

11. The method of claim 10, wherein in the step of providing a means for adsorbing an adsorbable reaction product, the solid is an effective amount of zeolite.

* * * * *

UNITED STATES PATENT AND TRADEMARK OFFICE
CERTIFICATE OF CORRECTION

PATENT NO.   : 6,159,432
DATED        : December 12, 2000
INVENTOR(S)  : Richard G. Mallinson and Lance Lobban It is certified that error appears in the above-identified patent and that said Letters Patent is hereby corrected as shown below:

Title page,
Item [75], Inventors, delete the name "Chang-jun Liu".

Drawings,
Please substitute new Fig. and 8 as follows:

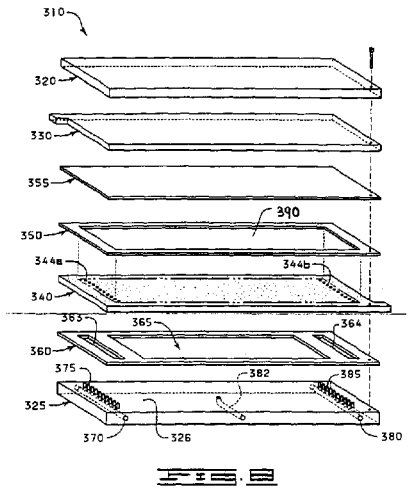

Column 4,
Line 12, delete "ZSM5 ," and subtitute therefore -- ZSM5, --.

Column 13,
Line 7, delete the second occurrence of the numeral "22" and substitute therefore the numeral -- 20 --.
Line 18, delete the phrase "assembly 12".

Column 14,
Line 19, delete "Sr/La2O3" and substitute therefore -- $Sr/La_2O_3$ --.
Lines 48 and 64, "sccm" and substitute therefore -- SCCM --.

Column 16,
Line 16, delete "750" and substitute therefore -- 750 --.
Lines 37 and 55, delete "space" and substitute therefore -- zone --.
Line 44, delete "space 395" and substitute therefore -- zone 390 --.

Column 18,
Lines 7 and 11, delete "330" and substitute therefore -- 330a --

UNITED STATES PATENT AND TRADEMARK OFFICE
CERTIFICATE OF CORRECTION

PATENT NO. : 6,159,432
DATED : December 12, 2000
INVENTOR(S) : Richard G. Mallinson and Lance Lobban It is certified that error appears in the above-identified patent and that said Letters Patent is hereby corrected as shown below:

Column 19,
Line 50, delete "345" and substitute therefore -- 346 --.
Line 52, delete "346" and substitute therefore -- 345 --.

Column 20,
Line 67, delete "or" and substitute therefore -- and --

Signed and Sealed this

Thirty-first Day of August, 2004

JON W. DUDAS
*Director of the United States Patent and Trademark Office*